United States Patent
Shishido et al.

(10) Patent No.: US 10,925,936 B2
(45) Date of Patent: Feb. 23, 2021

(54) VACCINE PHARMACEUTICAL COMPOSITION FOR CELL-MEDIATED IMMUNITY CONTAINING BISPHOSPHONATES

(71) Applicant: NITTO DENKO CORPORATION, Osaka (JP)

(72) Inventors: Takuya Shishido, Osaka (JP); Daisuke Asari, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/507,443

(22) PCT Filed: Sep. 2, 2015

(86) PCT No.: PCT/JP2015/074918
§ 371 (c)(1),
(2) Date: Feb. 28, 2017

(87) PCT Pub. No.: WO2016/035808
PCT Pub. Date: Mar. 10, 2016

(65) Prior Publication Data
US 2017/0360908 A1 Dec. 21, 2017

(30) Foreign Application Priority Data

Sep. 3, 2014 (JP) .............................. JP2014-179123

(51) Int. Cl.
| | |
|---|---|
| A61K 39/00 | (2006.01) |
| A61K 31/047 | (2006.01) |
| A61K 31/05 | (2006.01) |
| A61K 31/085 | (2006.01) |
| A61K 31/355 | (2006.01) |
| A61K 31/4184 | (2006.01) |
| A61K 31/4192 | (2006.01) |
| A61K 31/663 | (2006.01) |
| A61K 31/675 | (2006.01) |
| A61K 31/685 | (2006.01) |
| A61K 33/00 | (2006.01) |
| A61K 31/42 | (2006.01) |
| A61K 31/192 | (2006.01) |
| A61K 31/12 | (2006.01) |
| A61K 9/70 | (2006.01) |
| A61K 38/00 | (2006.01) |
| A61K 31/19 | (2006.01) |

(Continued)

(52) U.S. Cl.
CPC ........ *A61K 39/0005* (2013.01); *A61K 9/0014* (2013.01); *A61K 9/06* (2013.01); *A61K 9/7023* (2013.01); *A61K 9/7053* (2013.01); *A61K 9/7061* (2013.01); *A61K 31/047* (2013.01); *A61K 31/05* (2013.01); *A61K 31/085* (2013.01); *A61K 31/09* (2013.01); *A61K 31/12* (2013.01); *A61K 31/19* (2013.01); *A61K 31/192* (2013.01); *A61K 31/194* (2013.01); *A61K 31/196* (2013.01); *A61K 31/198* (2013.01); *A61K 31/216* (2013.01); *A61K 31/235* (2013.01); *A61K 31/352* (2013.01); *A61K 31/353* (2013.01); *A61K 31/355* (2013.01); *A61K 31/37* (2013.01); *A61K 31/375* (2013.01); *A61K 31/405* (2013.01); *A61K 31/407* (2013.01); *A61K 31/415* (2013.01); *A61K 31/4184* (2013.01); *A61K 31/4192* (2013.01); *A61K 31/42* (2013.01); *A61K 31/421* (2013.01); *A61K 31/4375* (2013.01); *A61K 31/4745* (2013.01); *A61K 31/5415* (2013.01); *A61K 31/616* (2013.01); *A61K 31/635* (2013.01); *A61K 31/663* (2013.01); *A61K 31/675* (2013.01); *A61K 31/685* (2013.01); *A61K 31/7048* (2013.01); *A61K 33/00* (2013.01); *A61K 33/04* (2013.01); *A61K 38/00* (2013.01); *A61K 38/10* (2013.01); *A61K 39/00* (2013.01); *A61K 45/06* (2013.01)

(58) Field of Classification Search
None
See application file for complete search history.

(56) References Cited

U.S. PATENT DOCUMENTS

| | | |
|---|---|---|
| 6,740,325 B1 | 5/2004 | Arnon et al. |
| 6,797,276 B1 | 9/2004 | Glenn et al. |

(Continued)

FOREIGN PATENT DOCUMENTS

| | | |
|---|---|---|
| CN | 103961307 A | 8/2014 |
| CN | 103961701 A | 8/2014 |

(Continued)

OTHER PUBLICATIONS

Duncan et al, Davies (ed.), Vaccine Adjuvants, Methods in Molecular Biology 626, Chapter 5, pp. 59-72, 2010.*

(Continued)

*Primary Examiner* — Brian Gangle
(74) *Attorney, Agent, or Firm* — Greenblum & Bernstein, P.L.C.

(57) ABSTRACT

The present invention aims to provide a vaccine pharmaceutical composition universally usable for induction of cellular immunity against various antigens and exerting a high cellular immunity inducing effect. The present invention relates to a vaccine pharmaceutical composition for inducing cellular immunity, containing: an antigen; and a first cellular immunity induction promoter that is a bisphosphonate.

20 Claims, 1 Drawing Sheet
Specification includes a Sequence Listing.

(51) Int. Cl.
*A61K 31/4375* (2006.01)
*A61K 9/00* (2006.01)
*A61K 45/06* (2006.01)
*A61K 31/415* (2006.01)
*A61K 31/196* (2006.01)
*A61K 9/06* (2006.01)
*A61K 31/09* (2006.01)
*A61K 31/194* (2006.01)
*A61K 31/198* (2006.01)
*A61K 31/216* (2006.01)
*A61K 31/235* (2006.01)
*A61K 31/352* (2006.01)
*A61K 31/353* (2006.01)
*A61K 31/37* (2006.01)
*A61K 31/375* (2006.01)
*A61K 31/405* (2006.01)
*A61K 31/407* (2006.01)
*A61K 31/421* (2006.01)
*A61K 31/4745* (2006.01)
*A61K 31/5415* (2006.01)
*A61K 31/616* (2006.01)
*A61K 31/635* (2006.01)
*A61K 31/7048* (2006.01)
*A61K 33/04* (2006.01)
*A61K 38/10* (2006.01)

(56) References Cited

U.S. PATENT DOCUMENTS

| 2005/0281832 | A1 | 12/2005 | Campbell et al. |
| 2007/0190169 | A1 | 8/2007 | Nieda et al. |
| 2008/0112974 | A1 | 5/2008 | Czerkinsky et al. |
| 2008/0193487 | A1 | 8/2008 | Schild et al. |
| 2009/0104161 | A1 | 4/2009 | Nieda et al. |
| 2009/0196887 | A1 | 8/2009 | Morita et al. |
| 2009/0202499 | A1 | 8/2009 | Zanetti et al. |
| 2009/0304744 | A1 | 12/2009 | Campbell et al. |
| 2013/0309270 | A1 | 11/2013 | Von Andrian et al. |
| 2014/0037694 | A1 | 2/2014 | Morimoto et al. |
| 2014/0220055 | A1 | 8/2014 | Okubo et al. |
| 2014/0220063 | A1 | 8/2014 | Asari et al. |

FOREIGN PATENT DOCUMENTS

| EP | 2762155 | A2 | 8/2014 |
| EP | 2762159 | A1 | 8/2014 |
| JP | 2002-504522 | A | 2/2002 |
| JP | 2002-531415 | A | 9/2002 |
| JP | 2007-516968 | A | 6/2007 |
| JP | 2009-523817 | A | 6/2009 |
| JP | 2010-259373 | A | 11/2010 |
| WO | 99/43350 | A1 | 9/1999 |
| WO | 2005/074460 | A3 | 8/2005 |
| WO | 2006/006638 | A1 | 1/2006 |
| WO | 2007/029689 | A1 | 3/2007 |
| WO | 2007/094924 | A2 | 8/2007 |
| WO | 2012/054807 | A2 | 4/2012 |
| WO | 2012/115222 | A1 | 8/2012 |

OTHER PUBLICATIONS

Paudel et al (Ther Deliv, 1:109-131, 2010).*
Extended European Search report from Application No. 15838615.1 dated Jan. 24, 2018.
Hosoi Akihiro et al., "Memory Th1 Cells Augment Tumor-Specific CTL following Transcutaneous Peptide mmunization", Cancer Research, 68, 2008, pp. 3941-3949.
Zhengrong Cui et al., "Bilayer Films for Mucosal (Genetic) Immunization via the Buccal Route in Rabbits", Pharmaceutical Research, vol. 19, No. 7, 2002, pp. 947-953.
International Search Report issued with respect to Application No. PCT/JP2015/074918, dated Nov. 17, 2015.
International Preliminary Report on Patentability issued with respect to Application No. PCT/JP20151074918, dated Mar. 7, 2017.
Office Action dated May 14, 2019 in corresponding Japanese Application. No. 2015-172940.
Office Action for CN App. No. 201580047564.3 dated Aug. 5, 2019 (w/ translation).
Office Action for CN App. No. 201580047564.3 dated Nov. 10, 2020 (w/ translation).

* cited by examiner

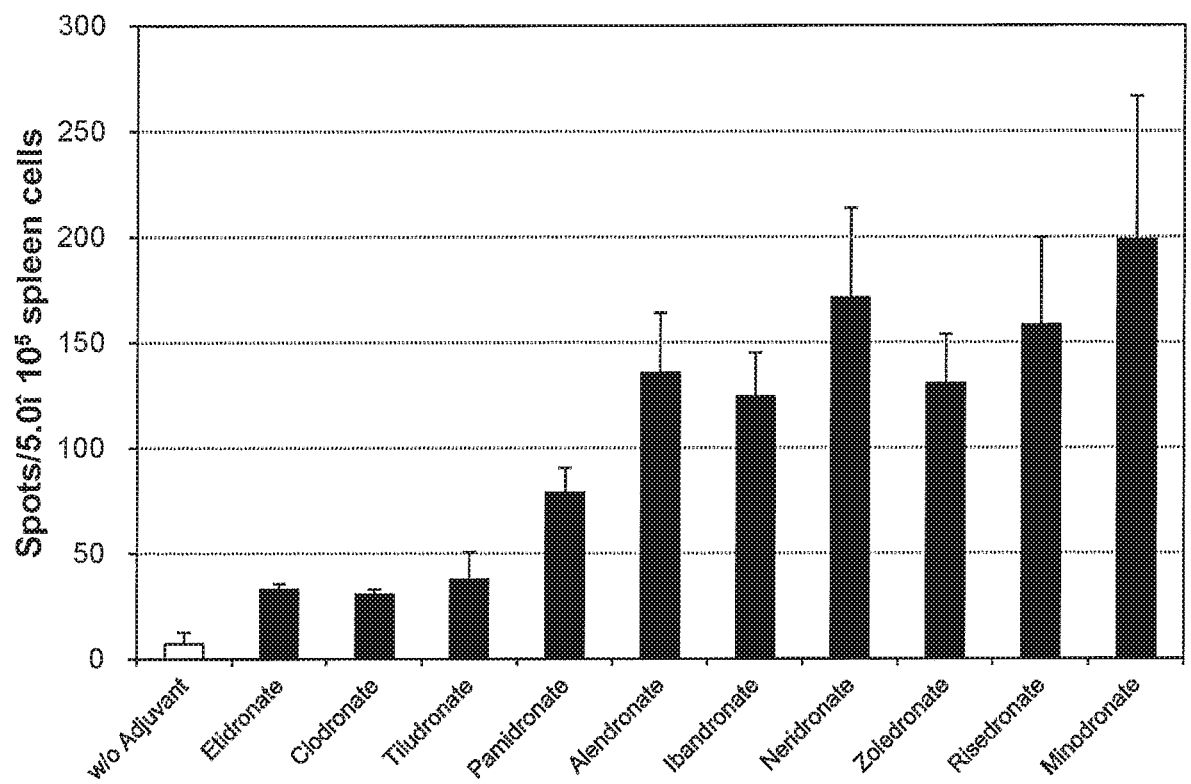

SEQUENCE LISTING

<160> NUMBER OF SEQ ID NOS: 16

<210> SEQ ID NO 1
<211> LENGTH: 9
<212> TYPE: PRT
<213> ORGANISM: Homo sapiens

<400> SEQUENCE: 1

Ala Tyr Ala Cys Asn Thr Ser Thr Leu
1               5

<210> SEQ ID NO 2
<211> LENGTH: 9
<212> TYPE: PRT
<213> ORGANISM: Homo sapiens

<400> SEQUENCE: 2

Glu Tyr Ile Leu Ser Leu Glu Glu Leu
1               5

<210> SEQ ID NO 3
<211> LENGTH: 9
<212> TYPE: PRT
<213> ORGANISM: Homo sapiens

<400> SEQUENCE: 3

Thr Tyr Leu Pro Thr Asn Ala Ser Leu
1               5

<210> SEQ ID NO 4
<211> LENGTH: 9
<212> TYPE: PRT
<213> ORGANISM: Homo sapiens

<400> SEQUENCE: 4

Ile Met Pro Lys Ala Gly Leu Leu Ile
1               5

<210> SEQ ID NO 5
<211> LENGTH: 9
<212> TYPE: PRT
<213> ORGANISM: Homo sapiens

<400> SEQUENCE: 5

Val Leu Gln Glu Leu Asn Val Thr Val
1               5

<210> SEQ ID NO 6
<211> LENGTH: 9
<212> TYPE: PRT
<213> ORGANISM: Homo sapiens

<400> SEQUENCE: 6

Lys Val Phe Gly Ser Leu Ala Phe Val
1               5

<210> SEQ ID NO 7
<211> LENGTH: 9
<212> TYPE: PRT
<213> ORGANISM: Homo sapiens

<400> SEQUENCE: 7

Lys Val Ala Glu Ile Val His Phe Leu
1               5

<210> SEQ ID NO 8
<211> LENGTH: 9
<212> TYPE: PRT
<213> ORGANISM: Homo sapiens

<400> SEQUENCE: 8

Lys Ile Phe Gly Ser Leu Ala Phe Leu
1               5

<210> SEQ ID NO 9
<211> LENGTH: 9
<212> TYPE: PRT
<213> ORGANISM: Homo sapiens

<400> SEQUENCE: 9

Ser Thr Ala Pro Pro Val His Asn Val
1               5

<210> SEQ ID NO 10
<211> LENGTH: 9
<212> TYPE: PRT
<213> ORGANISM: Hepatitis C virus

<400> SEQUENCE: 10

Asp Leu Met Gly Tyr Ile Pro Ala Val
1               5

<210> SEQ ID NO 11
<211> LENGTH: 9
<212> TYPE: PRT
<213> ORGANISM: Hepatitis B virus

<400> SEQUENCE: 11

Trp Leu Ser Leu Leu Val Pro Phe Val
1               5

<210> SEQ ID NO 12
<211> LENGTH: 15
<212> TYPE: PRT
<213> ORGANISM: Mycobacterium tuberculosis

<400> SEQUENCE: 12

Phe Gln Asp Ala Tyr Asn Ala Ala Gly Gly His Asn Ala Val Phe
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      Peptide-25B sequence

<400> SEQUENCE: 13

Phe Gln Asp Ala Tyr Asn Ala Val His Ala Ala His Ala Val Phe
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      PADRE sequence
<220> FEATURE:
<221> NAME/KEY: MOD_RES

```
<222> LOCATION: (1)..(1)
<223> OTHER INFORMATION: D-Alanine
<220> FEATURE:
<221> NAME/KEY: MOD_RES
<222> LOCATION: (3)..(3)
<223> OTHER INFORMATION: Cyclohexylalanine
<220> FEATURE:
<221> NAME/KEY: MOD_RES
<222> LOCATION: (13)..(13)
<223> OTHER INFORMATION: D-Alanine

<400> SEQUENCE: 14

Ala Lys Ala Val Ala Ala Trp Thr Leu Lys Ala Ala Ala
1               5                   10

<210> SEQ ID NO 15
<211> LENGTH: 20
<212> TYPE: DNA
<213> ORGANISM: Unknown
<220> FEATURE:
<223> OTHER INFORMATION: Description of Unknown:
      Bacterial DNA sequence

<400> SEQUENCE: 15
tccatgacgt tcctgacgtt                                              20

<210> SEQ ID NO 16
<211> LENGTH: 8
<212> TYPE: PRT
<213> ORGANISM: Gallus gallus

<400> SEQUENCE: 16

Ser Ile Ile Asn Phe Glu Lys Leu
1               5
```

VACCINE PHARMACEUTICAL COMPOSITION FOR CELL-MEDIATED IMMUNITY CONTAINING BISPHOSPHONATES

SEQUENCE LISTING

The instant application contains a Sequence Listing which has been submitted electronically in ASCII format and is hereby incorporated by reference in its entirety. Said ASCII copy, created on Jul. 11, 2017, is named P51784_SL.txt and is 3,218 bytes in size.

TECHNICAL FIELD

The present invention relates to a vaccine pharmaceutical composition for inducing cellular immunity.

BACKGROUND ART

Vaccines that are generally widely used aim to induce immunity for prevention of infectious diseases, and are used to administer pathogens (e.g., microorganisms and viruses) or a part thereof. Also, there are cancer vaccines for inducing specific attack of the immune system to cancer cells by allowing a cellular immune mechanism to recognize a cancer cell-specific antigen. These cancer vaccines are used as one of the means of treating cancer.

Injections, such as subcutaneous injection, intradermal injection, and intramuscular injection, are commonly used for administration of vaccines for immunization. Especially in the case of immunization for preventing of infectious diseases, invasive administration of vaccines into the body is commonly needed because microorganisms or viruses cannot enter the body through the skin due to their sizes.

Examples of adjuvants or immunostimulants practically used for immunization by injections include aluminum salts (e.g., aluminum hydroxide, aluminum phosphate, and aluminum chloride) and emulsions containing squalene (e.g., MF59® and AS03). Moreover, flagellar components, nucleic acids, cytokines, cationic polymers, polypeptides, and the like are also considered to be used as the adjuvants or immunostimulants.

Injections, however, have problems in terms of the quality of life (QOL) of the patients, such as pain, fear, needle marks and scarring thereof, and the burden of visiting the hospital in their daily life in a case where repeated administration is required. In particular, these problems are prominent in the case of cancer vaccines which are to be administered at a high frequency. Additionally, injections further have problems that only medical practitioners can give them, that the intradermal injection which gives a high immune effect requires a proficient skill to give, that medical practitioners are exposed to a risk of infection due to needle pricking, and that medical waste which necessitate special disposition, such as injection needles, is generated. The injection is therefore not necessarily the best administration route.

Most of the adjuvants or immunostimulants conventionally used for immunization by injections induce the humoral immunity that produces antibodies for prevention of infectious diseases. The use of a Th1-cytokine (e.g., GM-CSF, IL-2, IL-12, and IFN-γ) or an oil-based adjuvant that utilizes extended release of antigens to enhance the effect (e.g., Freund's adjuvant and MONTANIDE®) as an adjuvant for inducing cellular immunity (as a cellular immunity induction promoter) is considered but is not yet put into practical use. In addition, the number of kinds of such adjuvants is limited and the balance between the safety and the effect thereof is poor.

The administration route of vaccines other than injections may be, for example, transdermal administration (see Patent Literature 1 and Non-Patent Literature 1), buccal administration, transnasal administration, sublingual administration (see Non-Patent Literature 2 and Patent Literatures 2 and 3), or the like.

Since a large number of Langerhans cells that are antigen presenting cells are present in the skin, transdermal administration or transmucosal administration is now considered as a means to avoid various problems in relation to injections.

Examples of the adjuvant or immunistimulant considered to be used for immunization by transdermal administration or transmucosal administration include aluminum salts (e.g., aluminum hydroxide, aluminum phosphate, and aluminum chloride) and toxins (e.g., cholera toxin and *Escherichia coli* heat-labile toxin).

Most of the adjuvants or immunostimulants conventionally used for transdermal administration or transmucosal administration are those inducing humoral immunity. As the cellular immunity induction promoter, a few adjuvants such as toxins (e.g., cholera toxin, *Escherichia coli* heat-labile toxin) or nucleic acids have been reported.

Moreover, immunostimulants effectively used in induction of cellular immunity by transdermal administration of antigens have been hardly reported. In many cases, transdermal administration fails to give a sufficient cellular immunity inducing effect in comparison with the case of using injections.

Bisphosphonates used for treatment of osteoporosis have recently been found to stimulate dendritic cells or γδT cells to activate the immune response. Bisphosphates are now expected to have a new application as immunostimulants.

However, a sufficient therapeutic effect cannot be expected from simple administration of a bisphosphonate because the proportion of γδT cells in the peripheral blood is only 1% to 5%. As a means to achieve a sufficient effect, Patent Literatures 4, 5, and 6 each teaches immuno-cell therapy in which γδT cells isolated from the patient's peripheral blood is stimulated in vitro, co-cultured with other immunocompetent cell(s), and returned to the patient's blood.

Patent Literature 7, for example, reports a case where sufficient antibody production is induced by injecting a bisphosphonate to stimulate dendritic cells or the like several days before the administration of virus antigens as a vaccine.

CITATION LIST

Patent Literature

Patent Literature 1: US 2008/0193487 A
Patent Literature 2: JP 2002-531415 T
Patent Literature 3: US 2008/0112974 A
Patent Literature 4: WO 2006/006638
Patent Literature 5: WO 2007/029689
Patent Literature 6: JP 2010-259373 A
Patent Literature 7: WO 2012/054807

Non-Patent Literature

Non-Patent Literature 1: Hosoi Akihiro et al., Cancer Research, 68, 3941-3949 (2008)
Non-Patent Literature 2: Zhengrong Cui et al., Pharmaceutical Research, Vol. 19, No. 7, 947-953 (2002)

SUMMARY OF INVENTION

Technical Problem

The present invention aims to provide a vaccine pharmaceutical composition universally usable for induction of cellular immunity against various antigens and exerting a high cellular immunity inducing effect.

Solution to Problem

The present inventors noted that bisphosphonates used for treatment of osteoporosis can induce effective cellular immunity by stimulating dendritic cells or γδT cells in vitro.
The γδT cells secrete Th1 cytokines such as IFN-γ or TNF-α by antigenic stimulation to induce cellular immunity. However, since the proportion of the γδT cells in the peripheral blood is only 1% to 5%, simple administration of a bisphosphonate may not be able to induce sufficient cellular immunity.
In the mucosal epithelium and dermis, a large number of γδT cells are present and provide innate immunity by promptly reacting against foreign invasion.
The present inventors focused on this point to find out that a direct administration of a first cellular immunity induction promoter that is a bisphosphonate together with antigens to a living body by administration on a body surface (e.g., transdermal administration and transmucosal administration) can stimulate dendritic cells or γδT cells to effectively induce antigen-specific cellular immunity. The present inventors also found out that the additional use of a second cellular immunity induction promoter that is a helper peptide can further promote cellular immunity. The present inventors further found out that the additional use of an antioxidant and/or an anti-inflammatory drug that can suppress inflammation derived from a bisphosphonate can further promote cellular immunity.
It is to be noted that the findings obtained in vitro does not necessarily allow prediction of a reaction in vivo.
Specifically, the present invention relates to a vaccine pharmaceutical composition for inducing cellular immunity, containing: an antigen; and a first cellular immunity induction promoter that is a bisphosphonate.
The vaccine pharmaceutical composition of the present invention preferably further contains a second cellular immunity induction promoter that is a helper peptide.
The first cellular immunity induction promoter that is a bisphosphonate is preferably at least one selected from the group consisting of etidronate, clodronate, tiludronate, pamidronate, alendronate, ibandronate, neridronate, zoledronate, risedronate, and minodronate.
The vaccine pharmaceutical composition of the present invention preferably further contains an antioxidant and/or an anti-inflammatory drug.
The vaccine pharmaceutical composition of the present invention is preferably administered to a body surface.
The present invention is specifically described in the following.
The vaccine pharmaceutical composition of the present invention is used for inducing cellular immunity.

The cellular immunity inducing effect may be quantitatively determined by any method, and various methods are available. For example, the cellular immunity inducing effect can be determined by an immunity induction test using an animal model for immunological evaluation and the ELISPOT assay (IFN-γ). An exemplary sample for the ELISPOT assay is a spleen of an animal model for immunological evaluation.
The vaccine pharmaceutical composition of the present invention contains an antigen and a first cellular immunity induction promoter that is a bisphosphonate.
Containing the antigen and the first cellular immunity induction promoter that is a bisphosphonate, the vaccine pharmaceutical composition of the present invention can effectively induce antigen-specific cellular immunity.
As used herein, the term "antigen" refers to any substance that can induce immune response. The antigen is not limited, and examples thereof include proteins and peptides. In the case of transdermal administration in which an antigen is required to be skin permeable, use of an antigen having a small molecular weight is preferred. For example, a peptide having about 8 to about 12 amino acid residues can be used.
The antigen is not particularly limited, and examples thereof include a cancer antigen peptide and an antigen derived from an infectious pathogen.
As used herein, the term "cancer" refers to the abnormal expression of oncogene. Examples of the cancer include a cancer associated with overexpression, such as a hematopoietic tumor or solid cancer.
As used herein, the term "abnormal expression of a gene" means that the expression level of a gene in a cell is significantly increased or decreased by, for example, at least two times or at least four times, as compared to another cell in the same tissue.
As used herein, the term "overexpression" means an abnormal increase in the expression level. The expression level of a gene can be easily measured by any method known in the relevant technical field.
Examples of the oncogene include survivin gene, GPC3 gene, HER2/neu gene, MAGE-3 gene, MAGE-A1 gene, MAGE-A3/A6 gene, MAGE-A4 gene, MAGE-12 gene, proteinase-3 gene, AFP gene, CA-125 gene, CD44 gene, CEA gene, c-Kit gene, c-met gene, c-myc gene, L-myc gene, COX2 gene, CyclinD1 gene, Cytokeratin-7 gene, Cytokeratin-19 gene, Cytokeratin-20 gene, E2F1 gene, E2F3 gene, EGFR gene, Glil gene, hCGβ gene, HIF-1α gene, HnRNP A2/B1 gene, hTERT gene, MDM gene, MDR-1 gene, MMP-2 gene, MMP-9 gene, Muc-1 gene, Muc-4 gene, Muc-7 gene, NSE gene, ProGRP gene, PSA gene, RCAS1 gene, SCC gene, thymoglobulin gene, VEGF-A gene, and VEGF-A gene.
Non-limiting examples of cancers associated with abnormal expression of the survivin gene include malignant lymphoma, bladder cancer, lung cancer, and large bowel cancer. Non-liming examples of cancers associated with abnormal expression of the GPC3 gene include liver cancer, bile duct cancer, and stomach cancer. Non-liming examples of cancers associated with abnormal expression of the HER2/neu gene include breast cancer, stomach cancer, ovarian cancer, uterine cancer, bladder cancer, non-small cell lung cancer, and prostatic cancer. Non-liming examples of cancers associated with abnormal expression of the MAGE-3 gene include melanoma, lung cancer, head and neck cancer, bladder cancer, stomach cancer, esophageal cancer, and liver cancer. Non-liming examples of cancers associated with abnormal expression of the proteinase-3 gene include acute myelocytic leukemia and pancreatic cancer.

As used herein, the term "cancer antigen" refers to a substance such as a protein or peptide which is specifically expressed in tumor cells or cancer cells and capable of inducing cellular immune response.

As used herein, the term "cancer antigen peptide" refers to a partial peptide derived from a cancer antigen protein, capable of inducing cellular immune response. Usually, a cancer antigen peptide is produced by decomposition of a cancer antigen protein (which is an oncogene product) in a cancer cell, and is presented on the surface of a cancer cell by MHC class I molecules.

The cancer antigen peptide may be an endogenous cancer antigen peptide isolated and purified from cancer cells, or may be a synthetic peptide having the same amino acid sequence as the endogenous cancer antigen peptide. Specifically, preferred examples of the cancer antigen peptide include survivin 2B peptide, GPC3 peptide, HER2/neu_A24 peptide, MAGE3_A24 peptide, PR1 peptide, HER2/neu_A02 peptide, MAGE3_A02 peptide, HER2/neu_E75 peptide, MUC1 peptide, and altered peptides thereof.

As used herein, the term "survivin 2B peptide" refers to a peptide derived from survivin which is an oncogene product, having the sequence Ala Tyr Ala Cys Asn Thr Ser Thr Leu (SEQ ID No: 1).

As used herein, the term "GPC3 peptide" refers to a peptide derived from GPC3 which is an oncogene product, having the sequence Glu Tyr Ile Leu Ser Leu Glu Glu Leu (SEQ ID No: 2).

As used herein, the term "HER2/neu_A24 peptide" refers to an HLA-A24-restricted peptide derived from HER2/neu which is an oncogene product, having the sequence Thr Tyr Leu Pro Thr Asn Ala Ser Leu (SEQ ID No: 3).

As used herein, the term "MAGE3_A24 peptide" refers to an HLA-A24-restricted peptide derived from MAGE-3 which is an oncogene product, having the sequence Ile Met Pro Lys Ala Gly Leu Leu Ile (SEQ ID No: 4).

As used herein, the term "PR1 peptide" refers to a peptide derived from proteinase-3 which is an oncogene product, having the sequence Val Leu Gln Glu Leu Asn Val Thr Val (SEQ ID No: 5).

As used herein, the term "HER2/neu_A02 peptide" refers to an HLA-A02-restricted peptide derived from HER2/neu which is an oncogene product, having the sequence Lys Val Phe Gly Ser Leu Ala Phe Val (SEQ ID No: 6).

As used herein, the term "MAGE3_A02 peptide" refers to an HLA-A02-restricted peptide derived from MAGE-3 which is an oncogene product, having the sequence Lys Val Ala Glu Ile Val His Phe Leu (SEQ ID No: 7).

As used herein, the term "HER2/neu_E75 peptide" refers to a peptide derived from a product (HER2 protein) of an oncogene HER2/neu, having the sequence Lys Ile Phe Gly Ser Leu Ala Phe Leu (SEQ ID No: 8).

As used herein, the term "MUC1 peptide" refers to a peptide derived from MUC1 protein which is a glycoprotein that is highly expressed on many cancer cells, having the sequence Ser Thr Ala Pro Pro Val His Asn Val (SEQ ID No: 9).

As used herein, the term "altered peptide" refers to a peptide in which all or a part of amino acids are altered by, for example, substitution or modification.

The altered peptide is not particularly limited, and examples thereof include peptides such as: (a) a peptide having an amino acid sequence in which one to several amino acids (for example, 1, 2, 3, 4, or 5 amino acids) are substituted, deleted, or added in the amino acid sequence of the peptide; and (b) a peptide having an amino acid sequence in which all or a part of amino acids (for example, 1, 2, 3, 4, 5, 6, 7, 8, 9, or 10 amino acids) are modified in the amino acid sequence of the peptide.

The amino acids of the altered peptide may be modified in any manner. Examples of such modifications include acetylation; alkylation such as methylation; glycosylation; hydroxylation; carboxylation; aldehydation; phosphorylation; sulfonylation; formylation; aliphatic chain addition modification such as myristoylation, palmitoylation, and stearoylation; octanoylation; esterification; amidation; deamidation; disulfide bond formation modification such as cystine modification, glutathione modification, and thioglycolic acid modification; glycation; ubiquitination; succinimide formation; glutamylation; and prenylation.

The altered peptide may contain substitution, deletion, or addition of one or more amino acids and modification of one or more amino acids in combination.

As used herein, the term "infectious pathogen-derived antigen" refers to an infectious pathogen or its component or a substance derived from an infectious pathogen or its component, capable of inducing cellular immune response. Thus, it is possible to treat or prevent an infectious disease by administering the infectious pathogen-derived antigen together with the first cellular immunity induction promoter that is a bisphosphonate to a subject.

The infectious pathogen-derived antigen is preferably IPEP87 peptide, HBVenv peptide, or an altered peptide of IPEP87 peptide or HBVenv peptide.

As used herein, the term "IPEP87 peptide" refers to a peptide derived from a hepatitis C virus (HCV) protein, having the sequence Asp Leu Met Gly Tyr Ile Pro Ala Val (SEQ ID No: 10).

As used herein, the term "HBVenv peptide" refers to a peptide derived from a hepatitis B virus (HBV) protein, having the sequence Trp Leu Ser Leu Leu Val Pro Phe Val (SEQ ID No: 11).

As used herein, the term "infectious disease" refers to a disease caused by infection with an infectious pathogen, growth of an infectious pathogen, or the like.

The infectious disease is not particularly limited, and examples thereof include virus diseases caused by infection with viruses such as adenovirus (e.g., human adenovirus), herpesvirus (e.g., herpes simplex virus, varicella-zoster virus, cytomegalovirus, human herpesvirus, or Kaposi sarcoma-associated herpesvirus), picornavirus (e.g., polio virus, common cold virus, or hepatitis A virus), pox virus (e.g., smallpox virus, vaccinia virus, or molluscum contagiosum virus), picornavirus (e.g., rhinovirus or enterovirus), orthomyxovirus (e.g., influenza virus), paramyxovirus (e.g., parainfluenza virus, mumps virus, measles virus, respiratory syncytial virus (RSV), or Newcastle disease virus), parvovirus (e.g., adeno associated virus), togavirus (e.g., rubella virus), coronavirus (e.g., SARS coronavirus), hepadnavirus (e.g., hepatitis B virus), flavivirus (e.g., Japanese encephalitis virus, yellow fever virus, dengue virus, West Nile fever virus, St. Louis encephalitis virus, Murray Valley encephalitis virus, hepatitis C virus, or hepatitis G virus), hepevirus (e.g., hepatitis E virus), papillomavirus (e.g., human papilloma virus), calicivirus (e.g., Norovirus), rhabdovirus (e.g., rabies virus or vesicular stomatitis virus), filovirus (e.g., Ebola hemorrhagic fever virus), arenavirus (e.g., Lassa virus or hepatitis D virus), bunyavirus (e.g., California encephalitis virus or Rift Valley fever virus), reovirus (e.g., rotavirus), or retrovirus (e.g., human immunodeficiency virus (HIV) or adult T-cell leukemia virus); bacterial diseases such as those caused by infection with a bacterium such as *Escherichia*, *Enterobacter*, *Salmonella*, *Staphylococcus*, *dysentery bacillus*, *Listeria*, *Aerobacter*, *Helicobacter*, *Klebsiella*, *Proteus*, *Pseudomonas*, *Streptococcus*, *Chlamydia*, *Mycoplasma*, *Pneumococcus*, *Neisseria*, *Clostridium*, *Bacillus*, *Corynebacterium*, *Mycobacterium*, *Campyrobacter*, *Vibrio*, *Serratia*, *Providencia*, *Chromobacterium*, *Brucella*, *Yersinia*, *Haemophilus*, or *Bordetella*; fungous diseases such as *Chlamydia*, candidiasis, aspergillosis, histoplasmosis, and cryptococcal meningitis; malaria; *Pneumocystis carinii* pneumonia; leishmaniasis; cryptosporidiosis; toxoplasmosis; and *Trypanosoma* infection.

The peptides mentioned above can be in the free form or any pharmacologically acceptable salt form.

Examples of the pharmacologically acceptable salt form include acid salts (e.g., acetate, TFA salt, hydrochloride, sulfate, phosphate, lactate, tartrate, maleate, fumarate, oxalate, hydrobromate, succinate, nitrate, malate, citrate, oleate, palmitate, propionate, formate, benzoate, picrate, benzenesulfonate, dodecylsulfate, methanesulfonate, p-toluenesulfonate, glutarate, and various amino acid salts), metal salts (e.g., alkali metal salts (e.g., sodium salt and potassium salt), alkaline-earth metal salts (e.g., calcium salt and magnesium salt), and aluminum salt), and amine salts (e.g., triethylamine salt, benzylamine salt, diethanolamine salt, t-butylamine salt, dicyclohexylamine salt, arginine salt, dimethylammonium salt, and ammonium salt). In particular, acetate or TFA salt is preferred.

The peptides mentioned above can be synthesized or produced, isolated, and purified by a well-known method.

Examples of the first cellular immunity induction promoter that is a bisphosphonate include therapeutic agents for osteoporosis having a bisphosphonate skeleton and inhibiting bone resorption. Specific examples thereof include etidronate, clodronate, tiludronate, alendronate, ibandronate, pamidronate, neridronate, olpadronate, zoledronate, risedronate, minodronate, cimadronate, and incadronate. In terms of fewer side effects such as unfavorable stimulus to the site of administration or inflammation, preferred are etidronate, clodronate, and tiludronate which are referred to as first generation biophosphonates having no nitrogen atoms in the side chain. In terms of a high cellular immunity inducing effect, preferred are second generation biophosphonates (alendronate, ibandronate, pamidronate, neridronate, olpadronate) and third generation biophosphonates (zoledronate, risedronate, minodronate, cimadronate, incadronate) both having nitrogen atoms in the side chain. These compounds are each in a salt form.

In particular, the first cellular immunity induction promoter that is a bisphosphonate is more preferably at least one selected from the group consisting of etidronate, clodronate, tiludronate, pamidronate, alendronate, ibandronate, neridronate, zoledronate, risedronate, and minodronate.

As used herein, the term "salt" may refer to any organic or inorganic acid salt, and is preferably a pharmacologically acceptable salt.

As used herein, the term "pharmacologically acceptable salt" refers to a salt that does not have an adverse effect on the administration subject and does not eliminate the pharmacological activity of components of the vaccine pharmaceutical composition. Examples thereof include inorganic acid salts (e.g., hydrochloride, phosphate), organic acid salts (e.g., acetate, phthalate, TFA salt), metal salts such as alkali metal salts (e.g., sodium salt, potassium salt), alkaline earth metal salts (e.g., calcium salt, magnesium salt) and aluminum salt, and amine salts (e.g., triethylamine salt, benzylamine salt, diethanolamine salt, t-butylamine salt, dicyclohexylamine salt, arginine salt, dimethyl ammonium salt, ammonium salt).

The amount of the first cellular immunity induction promoter that is a bisphosphonate in the vaccine pharmaceutical composition of the present invention is not limited. The lower limit is preferably 0.001 parts by weight and the upper limit is preferably 1,000 parts by weight based on 1 part by weight of the antigen. When the amount is less than 0.001 parts by weight, the cellular immunity inducing effect may be insufficient. When the amount is more than 1,000 parts by weight, a safety problem may arise. The lower limit of the amount is more preferably 0.005 parts by weight and the upper limit thereof is more preferably 500 parts by weight. The lower limit is still more preferably 0.01 parts by weight and the upper limit is still more preferably 100 parts by weight.

The vaccine pharmaceutical composition of the present invention preferably further contains a second cellular immunity induction promoter that is a helper peptide.

The additional use of the second cellular immunity induction promoter that is a helper peptide can further promote cellular immunity.

As used herein, the term "helper peptide" refers to any peptide that activates helper-T cells.

Examples of the second cellular immunity induction promoter that is a helper peptide include a helper peptide derived from tubercle *bacillus*, a helper peptide derived from measles virus, a helper peptide derived from hepatitis B virus, a helper peptide derived from hepatitis C virus, a helper peptide derived from *Chlamydia trachomatis*, a helper peptide derived from *P. falciparum* sporozoite, a helper peptide derived from keyhole limpet haemocyanin, a helper peptide derived from tetanus toxin, a helper peptide derived from pertussis toxin, a helper peptide derived from diphtheria toxin, helper peptides derived from cancer cells (e.g., IMA-MMP-001 helper peptide, CEA-006 helper peptide, MMP-001 helper peptide, TGFBI-004 helper peptide, HER-2/neu(aa776-790) helper peptide, AE36 helper peptide, AE37 helper peptide, MET-005 helper peptide, and BIR-002 helper peptide), and universal helper analogs (e.g., PADRE), and altered peptides thereof. Preferred among these are Peptide-25, altered Peptide-25, and PADRE. Examples of the altered Peptide-25 include Peptide-25B.

As used herein, the term "Peptide-25" refers to a 15-amino acid peptide corresponding to amino acid residues 240 to 254 of Ag85B that is a key protein secreted by human tubercle *bacillus* (*Mycobacterium tuberculosis*) and having the sequence Phe Gln Asp Ala Tyr Asn Ala Ala Gly Gly His Asn Ala Val Phe (SEQ ID No: 12).

As used herein, the term "Peptide-25B" refers to a 15-amino acid peptide prepared by partially altering amino acids of Peptide-25 with an aim of enhancing the immunostimulation effect and having the sequence Phe Gln Asp Ala Tyr Asn Ala Val His Ala Ala His Ala Val Phe (SEQ ID No: 13).

As used herein, the term "PADRE" refers to a 13-amino acid peptide having the sequence D-Ala Lys cyclohexyl-Ala Val Ala Ala Trp Thr Leu Lys Ala Ala D-Ala (SEQ ID No: 14).

The amount of the second cellular immunity induction promoter that is a helper peptide in the vaccine pharmaceutical composition of the present invention is not limited. The lower limit is preferably 0.01 parts by weight and the upper limit is preferably 100 parts by weight based on 1 part by weight of the antigen. When the amount is less than 0.01 parts by weight, cellular immunity may not be sufficiently promoted. When the amount is more than 100 parts by weight, a safety problem may arise. The lower limit of the amount is more preferably 0.1 parts by weight and the upper limit thereof is more preferably 10 parts by weight.

The vaccine pharmaceutical composition of the present invention preferably further contains an antioxidant and/or an anti-inflammatory drug.

The antioxidant and/or the anti-inflammatory drug has an effect of suppressing inflammation caused by the bisphosphonate, and therefore, the additional use of the antioxidant and/or the anti-inflammatory drug can further promote cellular immunity.

As used herein, the term "antioxidant" refers to a substance that reduces or eliminates a harmful reaction involving oxygen. An antioxidant in conformity with the excipients listed in Japanese standards of medical package inserts may be used.

The antioxidant is not limited, and preferred is at least one selected from the group consisting of sodium nitrite, ascorbic acid, sodium hydrogen sulfite, cysteine hydrochloride, citric acid hydrate, dibutylhydroxytoluene (BHT), soybean lecithin, tocopherol, sodium pyrosulfite, dibutylhydroxyanisole (BHA), 1,3-butylene glycol, benzotriazole, propyl gallate, and 2-mercaptobenzimidazole. The antioxidant includes derivatives and pharmacologically acceptable salts of these antioxidants. For further promoting cellular immunity, more preferred among these are sodium nitrite, dibutylhydroxytoluene, soybean lecithin, sodium pyrosulfite, dibutylhydroxyanisole, and 2-mercaptobenzimidazole.

The amount of the antioxidant in the vaccine pharmaceutical composition of the present invention is not limited. The lower limit is preferably 0.01 parts by weight and the upper limit is 100 parts by weight based on 1 part by weight of the first cellular immunity induction promoter that is a bisphosphonate. When the amount is less than 0.01 parts by weight, the cellular immunity may not be sufficiently promoted. When the amount is more than 100 parts by weight, a safety problem may arise. The lower limit is more preferably 0.1 parts by weight and the upper limit is more preferably 50 parts by weight.

As used herein, the term "anti-inflammatory drug" refers to a substance suppressing inflammation.

The anti-inflammatory drug is not limited, and is preferably at least one selected from the group consisting of polyphenols, alkaloids, and phospholipase A2 inhibitors.

Examples of the polyphenol include naringenin, epicatechin, epigallocatechin, apigenin, chrysin, myricetin, rutin, quercetin, genistein, nobiletin, curcumin, resveratrol, and derivatives and pharmacologically acceptable salts of these. Examples of the alkaloid include coumarin, berberine, and derivatives and pharmacologically acceptable salts of these. Examples of the phospholipase A2 inhibitor include glycyrrhetinic acid and derivatives and pharmacologically acceptable salts thereof. For further promotion of cellular immunity, more preferred among these are epicatechin, chrysin, myricetin, resveratrol, coumarin, berberine, and glycyrrhetinic acid.

The anti-inflammatory drug is also preferably a cyclooxygenase inhibitor. As used herein, the term "cyclooxygenase inhibitor" refers to a substance that inhibits the function of cyclooxygenase (COX). Hereinafter, the "cyclooxygenase inhibitor" is also referred to as "COX inhibitor".

The COX inhibitor may selectively work on a specific cyclooxygenase (e.g., COX-1, COX-2) or have no such selectivity. The COX inhibitor is preferably at least one selected from the group consisting of cyclooxygenase non-selective inhibitors, cyclooxygenase-1 selective inhibitors, and cyclooxygenase-2 selective inhibitors.

Specific examples of the COX inhibitor include etodolac, loxoprofen, celecoxib, valdecoxib, parecoxib, lumiracoxib, meloxicam, tenoxicam, diclofenac, mefenamic acid, tolfenamic acid, flufenamic acid, meclofenamic acid, niflumic acid, benzydamine, indobufen, triflusal, tolmetin, fenoprofen, tiaprofenic acid, felbinac, nepafenac, amfenac, pravadoline, zaltoprofen, sulindac, nabumetone, diflunisal, piroxicam, ibuprofen, naproxen, fenoprofen, aspirin, methyl salicylate, salicylamide, salsalate, aloxiprin, tolmetin, indomethacin, proglumetacine, acemetacin, flurbiprofen, pranoprofen, acetaminophen, floctafenine, lornoxicam, tenoxicam, tiaprofenic acid, oxaprozin, ketoprofen, dexketoprofen, dexibuprofen, alminoprofen, ketorolac, mofezolac, phenylbutazone, oxyphenylbutazone, ketophenylbutazone, feprazone, sulfinbutazone, ethenzamide, tiaramide, tinoridine, epirizole, emorfazone, and derivatives thereof, as well as pharmacologically acceptable salts thereof. For further promotion of cellular immunity, preferred among these are loxoprofen, piroxicam, aspirin, and indomethacin.

The amount of the anti-inflammatory drug in the vaccine pharmaceutical composition of the present invention is not limited. The lower limit is preferably 0.01 parts by weight and the upper limit is preferably 100 parts by weight based on 1 part by weight of the first cellular immunity induction promoter that is a bisphosphonate. When the amount is less than 0.01 parts by weight, cellular immunity may not be sufficiently promoted. When the amount is more than 100 parts by weight, a safety problem may arise. The lower limit is more preferably 0.1 parts by weight and the upper limit is more preferably 50 parts by weight.

The vaccine pharmaceutical composition of the present invention may optionally contain additive(s). The additive(s) are used in accordance with the main component of the base, compatibility with the antigen and the first cellular immunity induction promoter that is a bisphosphonate, and the intended administration regimen. Examples thereof include tonicity agents, antiseptic bactericides, antioxidants, solubilizers, solubilizer aids, suspending agents, fillers, pH adjusters, stabilizers, absorption promoters, release rate controlling agents, colorants, plasticizers, crosslinking agents, and adhesives. These additives may be used alone or in combination of two or more thereof.

The vaccine pharmaceutical composition of the present invention is preferably administered to the body surface. More preferred is transdermal administration or transmucosal administration. The vaccine pharmaceutical composition of the present invention may also be administered intradermally, subcutaneously, or intramuscularly. In other words, the vaccine pharmaceutical composition of the present invention may be a vaccine pharmaceutical composition for intradermal, subcutaneous, or intramuscular administration, but is preferably a vaccine pharmaceutical composition for transdermal administration or transmucosal administration. Administration of the vaccine pharmaceutical composition of the present invention to the subject transdermally or transmucosally can effectively induce antigen-specific cellular immunity. In the case of transdermal administration, the administration may be noninvasive or minimally invasive administration.

As used herein, the term "subject" refers to any animal in which administration of the vaccine pharmaceutical composition in practical use may induce an immune response. Typically, the term refers to mammals including human, mouse, rat, canine, feline, leporine, equine, bovine, ovine, porcine, caprine, simian, and chimpanzee. A particularly preferred subject is a human.

<Vaccine Pharmaceutical Composition for Transdermal Administration>

The dosage form of the vaccine pharmaceutical composition for transdermal administration may be a solution for external application such as a liniment or a lotion; a spray for external application such as an aerosol; a gel; a patch such as a tape, or a poultice; an ointment, a plaster, or a cream. Categories, definitions, properties, production processes, and the like of these formulations are well known in the relevant art. For example, see the Japanese Pharmacopoeia, 16th Edition. Any known material may be used for these formulations.

Among the above dosage forms, preferred are a cream and a patch (tape, poultice).

The amounts of the antigen and the first cellular immunity induction promoter that is a bisphosphonate in the vaccine pharmaceutical composition for transdermal administration (in the case of a tape, in an adhesive layer) are not limited. The amount of the antigen is preferably 0.01 to 40% by weight, more preferably 0.1 to 30% by weight. The amount of the first cellular immunity induction promoter that is a bisphosphonate is preferably 0.001 to 30% by weight, more preferably 0.01 to 20% by weight.

Examples of a base used for the liniment include water, ethanol, fatty oils, hard paraffin, soft paraffin, liquid paraffin, glycerin, paraffin oil, beeswax, metal soap, mucilage, natural oils (such as almond oil, corn oil, peanut oil, castor oil, olive oil, and derivatives thereof (e.g., polyoxyl castor oil)), mutton tallow or derivatives thereof, and fatty acids and/or esters (e.g., stearic acid, oleic acid, and isopropyl myristate).

The lotion is a formulation containing ingredients (i.e., the antigen, the first cellular immunity induction promoter that is a bisphosphonate, and optionally, the second cellular immunity induction promoter) finely and homogeneously dispersed in an aqueous solution, and may be a suspension-type lotion or an emulsion-type lotion. Examples of the suspending agent include gum arabic, sodium alginate, sodium carboxymethyl cellulose, methylcellulose, and bentonite. Examples of the emulsifier include sodium lauryl sulfate and sorbitan fatty acid esters.

Examples of a base usable for the ointment include those commonly used as hydrophobic bases such as oils/fats, waxes, or hydrocarbon compounds. Specific examples of the base for the ointment include mineral bases such as yellow VASELINE®, white VASELINE®, paraffin, liquid paraffin, plastibase, and silicone, and animal or plant bases such as beeswax and animal or plant fats and/or oils.

Examples of a base usable for the cream include water/oil-type bases such as hydrophilic ointment and vanishing cream; and oil/water-type bases such as hydrophilic VASELINE®, purified lanolin, AQUAPHOR®, EUCERIN®, NEOCERIN, hydrous lanolin, cold cream, and hydrophilic plastibase.

Any base may be used for the gel. Examples thereof include hydrogel base such as carboxyvinyl polymers, gel bases, fat-free ointment, polyvinylpyrrolidone, polyvinyl alcohol, sodium polyacrylate, carboxymethyl cellulose, starch, xanthane gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl aminoacetate, casein, alkyl alginate ester, gelatin, and polyethylene glycol. Preferred is a hydrophilic base such as sodium polyacrylate because diffusion/release properties of the antigen are favorable.

Any base may be used for the poultice. Examples thereof include gelatin, sodium carboxymethyl cellulose, methylcellulose, sodium polyacrylate, kaolin, polyvinyl alcohol, polyvinylpyrrolidone, glycerin, propylene glycol, and water.

The tape preferably includes an adhesive layer containing ingredients (i.e., the antigen, the first cellular immunity induction promoter that is a bisphosphonate, and if necessary, the second cellular immunity induction promoter), and a support that supports the adhesive layer. The tape may further include a release liner that prevents exposure of the adhesive layer before use and that can be easily removed from the adhesive layer at the time of use.

Any adhesive may be used to form the adhesive layer. Examples of adhesives include acrylic adhesives containing acrylic polymers; rubber adhesives containing rubber elastomers; silicone adhesives such as silicone rubber, dimethylsiloxane adhesives, and diphenylsiloxane adhesives; vinyl ether adhesives such as polyvinyl methyl ether, polyvinyl ethyl ether, and polyvinyl isobutyl ether; vinyl ester adhesives such as vinyl acetate-ethylene copolymer; and polyester adhesives containing a carboxylic acid component (e.g., dimethyl terephthalate, dimethyl isophthalate, dimethyl phthalate), and a polyhydric alcohol component (e.g., ethylene glycol). Particularly preferred adhesives are acrylic adhesives, rubber adhesives, and silicone adhesives.

The amount of the adhesive in the adhesive layer is not limited, and is preferably 10 to 90% by weight, more preferably 20 to 80% by weight in terms of solids based on the total weight of the adhesive layer.

The acrylic adhesive preferably contains, as a main component, a polymer that contains alkyl (meth)acrylate as a first monomer.

Examples of the first monomer include alkyl (meth) acrylates having a C1-C18 linear, branched, or cyclic alkyl group. In particular, preferred are alkyl (meth)acrylates having a C4-C18 linear, branched, or cyclic alkyl group. Further, since a monomer component that lowers the glass transition temperature of a polymer is suitably used to impart adhesiveness at room temperature, an alkyl (meth) acrylate having a C4-C8 linear, branched, or cyclic alkyl group (e.g., butyl, pentyl, hexyl, cyclohexyl, heptyl, octyl, 2-ethylhexyl; preferably butyl, 2-ethylhexyl, or cyclohexyl; particularly preferably 2-ethylhexyl) is more preferred.

Specifically, the first monomer is preferably butyl acrylate, 2-ethylhexyl acrylate, 2-ethylhexyl methacrylate, cyclohexyl acrylate, or cyclohexyl methacrylate, particularly preferably 2-ethylhexyl acrylate. These first monomers may be used alone or in combination of two or more thereof.

The first monomer may be copolymerized with a second monomer. Such a second monomer may be a monomer having a functional group that can form a crosslinking point when a crosslinking agent is used. Examples of functional groups capable of being involved in crosslinking reactions include groups such as hydroxy, carboxy, and vinyl groups. Among these, hydroxy and carboxy groups are preferred.

Specific examples of the second monomer include hydroxyethyl (meth) acrylate, hydroxypropyl (meth) acrylate, N-hydroxyalkyl (meth)acrylamide, (meth)acrylic acid, itaconic acid, maleic acid, maleic anhydride, mesaconic acid, citraconic acid, and glutaconic acid. Among these, acrylic acid, methacrylic acid, hydroxyethyl acrylate (particularly, 2-hydroxyethyl acrylate) are preferred, and acrylic acid is the most preferred, in view of easy availability. These second monomers may be used alone or in combination of two or more thereof.

Moreover, the first monomer and second monomer may be further copolymerized with a third monomer.

Examples of the third monomer include vinyl esters such as vinyl acetate and vinyl propionate; vinyl ethers such as methyl vinyl ether and ethyl vinyl ether; vinyl amides such as N-vinyl-2-pyrrolidone and N-vinylcaprolactam; alkoxy (meth)acrylates such as methoxyethyl (meth) acrylate, ethoxyethyl (meth) acrylate, and tetrahydrofurfuryl (meth) acrylate; hydroxy group-containing monomers (as the third monomer, not as a crosslinking point) such as hydroxypropyl(meth)acrylate and α-hydroxymethyl acrylate; (meth) acrylic acid derivatives having an amide group such as (meth)acrylamide, dimethyl (meth)acrylamide, N-butyl (meth)acrylamide, and N-methylol (meth)acrylamide; aminoalkyl (meth)acrylates such as aminoethyl (meth)acrylate, dimethylaminoethyl (meth)acrylate, and t-butyl aminoethyl (meth)acrylate; alkoxyalkylene glycol (meth)acrylates such as methoxyethylene glycol (meth) acrylate, methoxydiethylene glycol (meth)acrylate, methoxypolyethylene glycol (meth)acrylate, and methoxypolypropylene glycol (meth) acrylate; (meth)acrylonitrile; monomers containing sulfonic acid such as styrenesulfonic acid, allylsulfonic acid, sulfopropyl(meth)acrylate, (meth)acryloyloxy naphthalene sulfonate, and acrylamide methylsulfonate; and vinyl group-containing monomers such as vinylpiperidone, vinylpyrimidine, vinylpiperazine, vinylpyrrole, vinylimidazole, vinyloxazole, and vinylmorpholine. Preferred among these are vinyl esters and vinyl amides. Vinyl acetate is preferred among vinyl esters, and N-vinyl-2-pyrrolidone is preferred among vinyl amides. These third monomers may be used alone or in combination of two or more thereof.

In the case of a copolymer of the alkyl (meth)acrylate (first monomer) and the vinyl monomer having a functional group capable of being involved in crosslinking reaction (second monomer), the alkyl (meth)acrylate and the vinyl monomer having a functional group capable of being involved in crosslinking reaction are preferably copolymerized at a weight ratio of (99-85):(1-15), more preferably at a weight ratio of (99-90):(1-10).

In the case of a copolymer of the alkyl (meth)acrylate (first monomer), the vinyl monomer having a functional group that can be involved in a crosslinking reaction (second monomer), and a different monomer other than these (third monomer), the alkyl (meth)acrylate, the vinyl monomer having a functional group capable of being involved in crosslinking reaction, and the different monomer are preferably copolymerized at a weight ratio of (40-94):(1-15):(5-50), more preferably at a weight ratio of (50-89):(1-10):(10-40).

The polymerization reaction may be carried out by any conventionally known method. For example, the above monomers may be reacted in the presence of an initiator (e.g., benzoyl peroxide or azobisisobutyronitrile) in a solvent (e.g., ethyl acetate) at 50° C. to 70° C. for 5 to 48 hours.

The acrylic adhesive preferably contains a 2-ethylhexyl acrylate/acrylic acid/N-vinyl-2-pyrrolidone copolymer, a 2-ethylhexyl acrylate/N-(2-hydroxyethyl)acrylamide/N-vinyl-2-pyrrolidone copolymer, a 2-ethylhexyl acrylate/2-hydroxyethyl acrylate/vinyl acetate copolymer, or a 2-ethylhexyl acrylate/acrylic acid copolymer, more preferably contains a 2-ethylhexyl acrylate/acrylic acid/N-vinyl-2-pyrrolidone copolymer.

The acrylic adhesive may be subjected to physical crosslinking treatment by radiation such as ultraviolet irradiation or electron beam irradiation, or chemical crosslinking treatment using various crosslinking agents such as an isocyanate compound (e.g., trifunctional isocyanate), an organic peroxide, an organic metal salt, a metal alcoholate, a metal chelate compound, or a polyfunctional compound (e.g., a polyfunctional external crosslinking agent, a polyfunctional monomer for internal crosslinking such as di(meth)acrylate).

Any rubber elastomer may be used for preparing the rubber adhesive, and examples thereof include polyisobutylene/polybutene elastomer, a styrene/diene/styrene block copolymer, styrene/butadiene elastomer, nitrile elastomer, chloroprene elastomer, vinylpyridine elastomer, polyisobutylene elastomer, butyl elastomer, and isoprene-butylene elastomer. Preferred among these are polyisobutylene (PIB) and a styrene/diene/styrene block copolymer (such as a styrene/butadiene/styrene block copolymer (SBS) or a styrene/isoprene/styrene block copolymer (SIS)), in view of solubility to the ingredients and the skin adhesiveness. These rubber elastomers may be used alone or in combination of two or more thereof.

In order to achieve appropriate adhesion and solubility to the ingredients, the rubber adhesive may be a mixture of rubber elastomers formed from the same or different components and different in the average molecular weight. For example, a mixture of a high-molecular-weight polyisobutylene having an average molecular weight of 150,000 to 5,500,000 and a medium-molecular-weight polyisobutylene having an average molecular weight of 10,000 to 150,000 and/or a low-molecular-weight polyisobutylene having an average molecular weight of 500 to 4,000 is preferred. The amount of the high-molecular-weight polyisobutylene is 10 to 80% by weight, preferably 20 to 70% by weight, relative to the total amount of the polyisobutylenes. The amount of the medium-molecular-weight polyisobutylene is 0 to 90% by weight, preferably 10 to 80% by weight, relative to the total amount of the polyisobutylenes. The amount of the low-molecular-weight polyisobutylene is 0 to 80% by weight, preferably 10 to 60% by weight, relative to the total amount of the polyisobutylenes.

As user herein, the term "average molecular weight" refers to a viscosity average molecular weight calculated from the Flory viscosity equation. The average molecular weight is determined by calculating the Staudinger index ($J_0$) from the flow time at 20° C. of the capillary 1 of an Ubbelohde viscometer by the Schulz-Blaschke equation, and using this $J_0$ value in the following expression.

$$J_0 = \eta_{sp}/c(1+0.31\eta_{sp}) \quad \text{(Schulz-Blaschke equation)}$$

$$\eta_{sp} = t/t_0 - 1$$

t: Flow time of solution (according to Hagenbach-couette correction formula)

$t_0$: Flow time of solvent (according to Hagenbach-couette correction formula)

c: Concentration of solution (g/cm³)

$$J_0 = 3.06 \times 10^{-2} \overline{Mv}^{0.65}$$

Mv: Viscosity average molecular weight

In order to provide appropriate tackiness, the rubber adhesive may contain a tackifier such as rosin resin, polyterpene resin, coumarone-indene resin, petroleum resin, terpene-phenol resin, xylene resin, or alicyclic saturated hydrocarbon resin. These tackifiers may be used alone or in combination of two or more thereof.

The amount of the tackifier is preferably 50% by weight or less, more preferably 5 to 40% by weight based on the total weight of the rubber adhesive.

Examples of the silicone adhesive include polyorganosiloxane adhesives, polydimethylsiloxane adhesives, and polydimethyldiphenyl-siloxane adhesives. In particular, commercially available silicone adhesives such as BIO PSA (Dow Corning Corporation) are preferred.

The adhesive layer may further contain a skin permeation enhancer.

As used herein, the term "skin permeation enhancer" refers to any substance that may improve the efficiency of skin permeation of a transdermally administered antigen.

The skin permeation enhancer is preferably liquid (i.e., having fluidity) at room temperature (25° C.). In the case where two or more kinds of skin permeation enhancers are mixed, the final mixture is preferably liquid at room temperature (25° C.) and has an effect of enhancing skin permeation. Such an organic liquid component is preferably a hydrophobic liquid component in terms of the compatibility in the adhesive.

Examples of the skin permeation enhancer include higher alcohols, fatty acid esters, and polyhydric alcohol fatty acid esters.

The higher alcohol is preferably a C8-C18 higher alcohol, more preferably a C8-C14 higher alcohol. The fatty acid ester is preferably a fatty acid ester of a C8-C18 fatty acid and a C1-C18 monohydric alcohol, more preferably a fatty acid ester of a C12-C16 fatty acid and a C1-C18 monohydric alcohol. In particular, preferred are fatty acid esters, and particularly preferred are isopropyl myristate, isopropyl palmitate, and diethyl sebacate.

Specific examples of the skin permeation enhancer include higher alcohols such as oleyl alcohol and octyldodecanol; polyhydric alcohols such as glycerin, ethylene glycol, and polypropylene glycol; higher fatty acids such as oleic acid and caprylic acid; fatty acid esters such as isopropyl myristate, isopropyl palmitate, and ethyl oleate; polybasic acid esters such as diethyl sebacate and diisopropyl adipate; polyhydric alcohol fatty acid esters such as diglyceryl triisostearate, sorbitan monooleate, propylene glycol dicaprylate, polyethylene glycol monolaurate, and polyoxyethylene sorbitol tetraoleate; polyoxyethylene alkyl ethers such as polyoxyethylene lauryl ether; hydrocarbons such as squalane or liquid paraffin; vegetable oils such as olive oil and castor oil; silicone oil; pyrrolidones such as N-methylpyrrolidone and N-dodecyl pyrrolidone; and sulfoxides such as decyl methyl sulfoxide. These skin permeation enhancers may be used alone or in combination of two or more thereof.

In the case of using the acrylic adhesive or rubber adhesive, the skin permeation enhancer used may be, for example, polyvinyl pyrrolidone, crospovidone, polypropylene glycol, polyvinyl alcohol, carboxy vinyl polymer, hydroxypropyl cellulose, or a mixture of these. Preferred among these are polyvinyl pyrrolidone, crospovidone, and polypropylene glycol.

The amount of the skin permeation enhancer in the adhesive layer is not limited, and is preferably 0.1 to 70% by weight, more preferably 1 to 65% by weight, still more preferably 5 to 60% by weight, based on the total weight of the adhesive layer. When the amount of the skin permeation enhancer is 0.1% by weight or more, the effect of promoting skin permeation is high. When the amount of the skin permeation enhancer is 70% by weight or less, the effect of promoting skin permeation is high, while reduction in the adhesion and the cohesion of the entire adhesive layer is suppressed.

The adhesive layer may have any thickness. Preferably, the thickness is 10 to 1,000 µm. With the thickness within the above range, the adhesive layer can readily contain the ingredients each in an effective amount and exhibit sufficient adhesion. Moreover, the adhesive layer with such a thickness can be readily formed.

The support is not limited, and is preferably one substantially impermeable to the above ingredients. In other words, it is preferably one that prevents a decrease in the amount of the antigen, the first cellular immunity induction promoter that is a bisphosphonate, and optionally the second cellular immunity induction promoter contained in the adhesive layer by not allowing them to pass through the support and escape from the back side.

The support may be a single film of polyester, polyamide, polyvinylidene chloride, polyethylene, polypropylene, polyvinyl chloride, ethylene-ethyl acrylate copolymer, polytetrafluoroethylene, ionomer resin, metal foil, or the like, or it may be a laminated film of these mentioned above. Preferred among these is a laminated film of a nonporous plastic film which is made of any of the above-mentioned materials and a porous film, in view of achieving good adhesiveness (anchoring properties) between the support and the adhesive layer. In this case, the adhesive layer is preferably formed on the porous film side.

Any porous film that improves the anchoring properties between the support and the adhesive layer may be used. Examples thereof include paper, woven fabrics, nonwoven fabrics, knitted fabrics, and mechanically perforated sheets. Preferred among these are paper, woven fabrics, and nonwoven fabrics, in view of factors such as handleability. A porous film having a thickness in the range of 1 to 200 µm is preferably employed in view of improving anchoring properties and also in view of factors such as flexibility and attachment operability of the tape. In addition, in the case where the porous film is a woven fabric or a nonwoven fabric, the weight per unit area is preferably 5 to 30 g/m$^2$, more preferably 6 to 15 g/m$^2$.

A suitable support is a laminated film of a polyester film (preferably, a polyethylene terephthalate film) having a thickness of 1.5 to 6 µm and a polyester (preferably, polyethylene terephthalate) nonwoven fabric having a weight per unit area of 6 to 15 g/m$^2$.

The release liner is not limited as long as it is preliminarily subjected to release treatment and ensures sufficiently light releasability. Examples thereof include films made of polyester, polyvinyl chloride, polyvinylidene chloride, polyethylene terephthalate, or the like; paper such as wood-free paper and glassine paper; and laminate films of wood-free paper or glassine paper and polyolefin, which are preliminarily treated to be releasable by applying, for example, silicone resin or fluorine resin to the surface to be in contact with the adhesive layer.

The thickness of the release liner is preferably 10 to 200 µm, more preferably 25 to 100 µm.

The release liner is preferably formed from polyester (in particular, polyethylene terephthalate) resin in view of factors such as barrier and cost. In this case, the thickness of the release liner is preferably about 25 to 100 μm in view of handleability.

<Vaccine Pharmaceutical Composition for Transmucosal Administration>

Examples of transmucosal administration include sublingual administration, transnasal administration, buccal administration, rectal administration, and vaginal administration.

The dosage form of the vaccine pharmaceutical composition for transmucosal administration may be, for example, a semisolid formulation such as a gel (jelly), a cream, an ointment, or a plaster; a solution; a solid formulation such as a powder, a fine granule, a granule, a film, a tablet, or an orally disintegrating tablet; a mucosal spray formulation such as an aerosol; or an inhalant. Categories, definitions, properties, production processes, and the like of these formulations are well known in the relevant art. For example, see the Japanese Pharmacopoeia, 16th Edition. Any known material may be used for these formulations.

The amounts of the antigen and the first cellular immunity induction promoter that is a bisphosphonate in the vaccine pharmaceutical composition for transmucosal administration are not limited. The amount of the antigen is preferably 0.01 to 40% by weight, more preferably 0.1 to 30% by weight. The amount of the first cellular immunity induction promoter that is a bisphosphonate is preferably 0.001 to 30% by weight, more preferably 0.01 to 20% by weight.

A solvent usable for the solution may be, for example, an appropriate amount of water, ethanol, glycerin, or propylene glycol. The solution can be prepared by dispersing or dissolving the ingredients mentioned above in any of these solvents.

Any base may be used for the gel (jelly). Examples thereof include hydrogel base such as carboxyvinyl polymers, gel bases, fat-free ointment, polyvinylpyrrolidone, polyvinyl alcohol, sodium polyacrylate, carboxymethyl cellulose, starch, xanthane gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, EUDRAGIT®, casein, alkyl alginate ester, gelatin, and polyethylene glycol. A fluidic gel and a formable gel can be prepared by dissolving any of these bases in a solvent and adding the above ingredients thereto. The solvent is preferably water. Glycerin, propylene glycol, or the like can also be used. A hydrophilic base such as sodium polyacrylate is preferred because diffusion/release properties of the antigen are favorable.

Examples of a base used for the cream include water/oil-type bases such as hydrophilic ointment and vanishing cream; and oil/water-type bases such as hydrophilic VASELINE®, purified lanolin, AQUAPHOR®, EUCERIN®, NEOCERIN, hydrous lanolin, cold cream, and hydrophilic plastibase. A cream can be prepared by stirring any of these bases in an oil/fat solvent or water at high speed using a homogenizer or the like and adding the above ingredients thereto.

Examples of a base used for the film include polyvinylpyrrolidone, polyvinyl alcohol, sodium polyacrylate, carboxymethyl cellulose, starch, xanthane gum, karaya gum, sodium alginate, methylcellulose, carboxyvinyl polymer, agar, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethyl aminoacetate, casein, and alkyl alginate ester. A film can be prepared by dissolving any of these bases in water or an organic polar solvent such as ethanol, adding the above ingredients thereto, and applying the resulting material to form a thin film, followed by drying.

A hydrophilic base such as sodium polyacrylate is preferred because diffusion/release properties of the antigen are favorable.

Examples of additives for the powder, fine granule, granule, tablet, and the like include excipients such as lactose, corn starch, and crystalline cellulose, and bonding agents such as hydroxypropyl cellulose and gum arabic. The powder, fine granule, granule, tablet, or the like can be prepared by adding these additives to an appropriate amount of water or a solvent such as ethanol, adding the above ingredients thereto, mixing and stirring the mixture, and performing a combination of processes such as granulation, drying, and tableting. If needed, a lubricant such as magnesium stearate or a coating agent such as hydroxypropyl cellulose or sucrose can also be added.

Examples of the base usable for the orally disintegrating tablet (freeze dry type) include polysaccharides such as gelatin and pullulan. In addition, mannitol, trehalose, sorbitol, glycine, or the like may be used as a forming aid. The orally disintegrating tablet (freeze dry type) can be prepared by dissolving any of these bases and forming aids in water, adding the above ingredients, dispensing and freeze drying the resulting material.

The aerosol may contain, for example, a solution, a gel having high fluidity, a cream, or fine powder such as a powdered drug. Dispersing the content as solid or liquid microparticles in a gas using a spray device enables effective administration to an administration site such as the oral mucosa or the nasal mucosa.

<Vaccine Pharmaceutical Composition for Intradermal, Subcutaneous, or Intramuscular Administration>

The dosage form of the vaccine pharmaceutical composition for intradermal, subcutaneous, or intramuscular administration is an injectable form with a certain level of fluidity, and may be, for example a solution, a water-soluble or hydrophobic suspension, or a cream. Categories, definitions, properties, production processes, and the like of these formulations are well known in the relevant art. For example, see the Japanese Pharmacopoeia, 16th Edition. Any known material may be used for these formulations.

The amounts of the antigen and the first cellular immunity induction promoter that is a bisphosphonate in the vaccine pharmaceutical composition for intradermal, subcutaneous, or intramuscular administration are not limited. The amount of the antigen is preferably 0.01 to 40% by weight, more preferably 0.1 to 30% by weight. The amount of the first cellular immunity induction promoter that is a bisphosphonate is preferably 0.001 to 30% by weight, more preferably 0.01 to 20% by weight.

A solvent usable for the solution may be an appropriate amount of water, saline, ethanol, glycerin, propylene glycol, or the like. The solution can be prepared by dispersing or dissolving the above ingredients in any of these solvents.

Any base may be used for the water-soluble suspension, and examples thereof include a hydrogel base such as carboxy vinyl polymers, gel bases, fat-free ointment, polyvinylpyrrolidone, polyvinyl alcohol, sodium polyacrylate, carboxymethyl cellulose, starch, xanthan gum, karaya gum, sodium alginate, methylcellulose, hydroxypropyl cellulose, hydroxypropyl methylcellulose phthalate (HPMCP), cellulose acetate phthalate (CAP), carboxymethyl ethyl cellulose (CMEC), ethylcellulose, hydroxyethylcellulose, hydroxypropyl methylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethyl cellulose, sodium carboxymethyl cellulose, calcium carboxymethyl cellulose, pullulan, chitosan, sodium carboxymethyl starch, *Plantago testa*, galactomannan, EUDRAGIT®, casein, alkyl alginate, gelatin, or polyethylene glycol. A fluidic suspension can be prepared by dissolving any of these bases in a solvent and adding the above ingredients. The solvent is preferably saline, and may also be glycerin, propylene glycol, or the like.

A hydrophilic base such as sodium polyacrylate is preferred because diffusion/release properties of the antigen are favorable.

Examples of the base usable for the hydrophobic suspension include water/oil-type bases such as hydrophilic ointment and vanishing cream; and oil/water-type bases such as hydrophilic VASELINE®, purified lanolin, AQUAPHOR®, EUCERIN®, NEOCERIN, hydrous lanolin, cold cream, and hydrophilic plastibase. The oil/fat suspension can be prepared by stirring any of these bases in an oil/fat solvent or water with a homogenizer at high speed and adding the above ingredients.

In administration of the vaccine pharmaceutical composition of the present invention to the subject, the therapeutically effective amount of the antigen may widely vary depending on the severity of the disease, age and relative health of the subject, and other known factors. Generally, satisfactory results can be obtained at a dose of about 0.1 µg to 1 g/kg body weight per day. The first cellular immunity induction promoter that is a bisphosphonate is simultaneously or sequentially administered with the antigen. Simultaneous administration is preferred.

The therapeutically effective amount of the first cellular immunity induction promoter that is a bisphosphonate may widely vary depending on the specific type of the bisphosphonate used and the presence or absence of other cellular immunity induction promoter(s). Generally, satisfactory results can be obtained at about 0.01 µg to 1 g/kg body weight per day.

The daily dose may be administered in one time, or may be split into multiple doses (i.e., two or more doses, for example, 2, 3, 4, or 5 doses). Preferably, the period of continuous administration per dose is appropriately determined in the range from 1 minute to 7 days. Preferably, the administration interval is appropriately selected from once a day to once a year (for example, once a day, once every 2 days, once every 3 days, once a week, once every 2 weeks, once a month, once every 3 months, once every 6 months, once a year, etc.), or longer administration intervals, depending on the condition of patients, severity of the disease, and whether it is for therapeutic purposes or preventive purposes. Generally, for the therapeutic purposes for a patient actually having a severe disease, the vaccine pharmaceutical composition of the present invention is preferably administered at a higher frequency and/or in a higher dose, while for the preventive purposes for patients not having a disease, the vaccine pharmaceutical composition of the present invention is preferably administered at a lower frequency and/or in a lower dose.

Advantageous Effects of Invention

Since allowing the noninvasive administration to the body surface (e.g., transdermal administration or transmucosal administration), the vaccine pharmaceutical composition of the present invention can provide the following advantages. Specifically, excellent compliance owing to noninvasive administration (e.g., transdermal administration or transmucosal administration) or minimally invasive administration (e.g., administration to the skin surface after corneum exfoliation such as tape stripping, or corneum perforation such as micro needling or electroporation) is achieved; patients are free from pain or fear of injections; patients can perform administration by themselves as the administration is easy; medical practitioners can avoid a risk of infection due to needle pricking; in a case where repetitive administration is needed, the ambulatory frequency can be reduced to contribute to the improvement in quality of life of the patient; and medical wastes (e.g., needles) which necessitate special disposition are not generated.

In the case of the vaccine pharmaceutical composition of the present invention in the form of a patch such as a tape or a poultice, it is advantageous in that a predetermined dose can be reliably administered; the drug release rate can be controlled at any rate; and the drug is prevented from being attached to a site other than the intended site. In addition, since a patch is easily detachable, it is advantageous in that patients can immediately discontinue administration on their own by removing the patch from the site of application when an adverse effect occurs, for example.

Administration of the vaccine pharmaceutical composition of the present invention gives a significantly improved cellular immunity inducing effect compared to administration of the antigen alone. The use of the vaccine pharmaceutical composition of the present invention for non-invasive administration to the body surface (e.g., transdermal administration or transmucosal administration) can induce stronger immunity compared to administration by injections. Moreover, the vaccine pharmaceutical composition of the present invention further containing an antioxidant and/or an anti-inflammatory drug has a synergistically enhanced cellular immunity inducing effect.

BRIEF DESCRIPTION OF DRAWINGS

FIG. 1 is a graph showing the cellular immunity inducing effect upon transdermal administration of creams for transdermal administration obtained in Examples 1 to 10 and Comparative Example 2.

DESCRIPTION OF EMBODIMENTS

The present invention is described specifically in detail in the following with reference to, but not limited to, examples.

Examples 1 to 64, Comparative Examples 1 to 51

(Preparation of Creams for Transdermal Administration)

Creams for transdermal administration having a composition as shown in Tables 1 to 4 and 6 were prepared. Specifically, an antigen peptide, a first cellular immunity induction promoter that is a bisphosphonate, and if needed, a second cellular immunity induction promoter that is a helper peptide, an antioxidant, and an anti-inflammatory drug (including COX inhibitor) mentioned below, and 15% by weight of dimethyl sulfoxide (DMSO) were mixed in amounts specified in Tables 1 to 4 and 6. To the resulting mixture, a base (base cream) was added to obtain a total weight of 100% by weight, and mixed to give a cream for transdermal administration. The base cream used was prepared by mixing materials shown in Table 5 in amounts as specified. White VASELINE®, sorbitan monostearate, isostearic acid, benzyl alcohol, stearyl alcohol, polysorbate 60, concentrated glycerin, and dimethyl sulfoxide (DMSO) were purchased from Wako Pure Chemical Industries, Ltd. Cetanol was purchased from Tokyo Chemical Industry Co., Ltd.

A PET film/PET nonwoven fabric laminate (area: 0.7 cm$^2$) was attached to the center of an adhesive tape for fixing in such a manner that the PET film is in contact with the tape, thereby preparing a complex base. To a nonwoven fabric portion of the obtained complex base, 4 mg of the cream for transdermal administration was applied. This was used as an administration sample in an immunity test.

(First cellular immunity induction promoter that is a bisphosphonate)
    Etidronate (LKT Labolatories, Inc.)
    Clodronate (LKT Labolatories, Inc.)
    Tiludronate (Sigma-Aldrich Co. LLC)
    Pamidronate (Tokyo Chemical Industry Co., Ltd.)
    Alendronate (Medichem)
    Ibandronate (URQUIMA S.A.)
    Neridronate (Sigma-Aldrich Co. LLC)
    Zoledronate (Konan Chemical Industry co., ltd.)
    Risedronate (Propharma S.A.)
    Minodronate (Ava Chem Scientific)

(Antioxidant)
    Sodium nitrite (Wako Pure Chemical Industries, Ltd.)
    Ascorbic acid (Wako Pure Chemical Industries, Ltd.)
    Sodium hydrogen sulfite (Wako Pure Chemical Industries, Ltd.)
    Cysteine hydrochloride (Kyowa Hakko Bio Co., Ltd.)
    Citric acid hydrate (Komatsuya Corporation)
    BHT (dibutylhydroxytoluene, Wako Pure Chemical Industries, Ltd.)
    Soybean lecithin (Wako Pure Chemical Industries, Ltd.)
    Tocopherol (Kanto Chemical Co., Inc.)
    Sodium pyrosulfite (Wako Pure Chemical Industries, Ltd.)
    BHA (dibutylhydroxyanisole, Kanto Chemical Co., Inc.)
    1,3-butylene glycol (1,3-butanediol, Wako Pure Chemical Industries, Ltd.)
    Benzotriazole (Wako Pure Chemical Industries, Ltd.)
    Propyl gallate (DSP Gokyo Food & Chemical Co., Ltd.)
    2-MBI (2-mercaptobenzimidazole, Wako Pure Chemical Industries, Ltd.)

(Anti-Inflammatory Drug)
    Naringenin (polyphenol, LKT Labolatories, Inc.)
    Epicatechin (polyphenol, Wako Pure Chemical Industries, Ltd.)
    Apigenin (polyphenol, Wako Pure Chemical Industries, Ltd.)
    Chrysin (polyphenol, Wako Pure Chemical Industries, Ltd.)
    Myricetin (polyphenol, Wako Pure Chemical Industries, Ltd.)
    Rutin (polyphenol, Wako Pure Chemical Industries, Ltd.)
    Genistein (polyphenol, Wako Pure Chemical Industries, Ltd.)
    Nobiletin (polyphenol, Wako Pure Chemical Industries, Ltd.)
    Curcumin (polyphenol, Wako Pure Chemical Industries, Ltd.)
    Resveratrol (polyphenol, Wako Pure Chemical Industries, Ltd.)
    Coumarin (alkaloid, Wako Pure Chemical Industries, Ltd.)
    Berberine (berberine chloride n-hydrate, alkaloid, Wako Pure Chemical Industries, Ltd.)
    Glycyrrhetinic acid (phospholipase A2 inhibitor, Wako Pure Chemical Industries, Ltd.)

(COX inhibitor (anti-inflammatory drug))
    Etodolac (Wako Pure Chemical Industries, Ltd.)
    Loxoprofen (loxoprofen Na, Yoshindo Inc.)
    Diclofenac (diclofenac sodium, Wako Pure Chemical Industries, Ltd.)
    Celecoxib (Sigma-Aldrich Co., LLC)
    Valdecoxib (Sigma-Aldrich Co., LLC)
    Piroxicam (Sigma-Aldrich Co., LLC)
    Aspirin (acetylsalicylic acid, Wako Pure Chemical Industries, Ltd.)
    Indomethacin (Wako Pure Chemical Industries, Ltd.)
    Ketoprofen (Wako Pure Chemical Industries, Ltd.)
    Ibuprofen (Wako Pure Chemical Industries, Ltd.)
    Naproxen (Wako Pure Chemical Industries, Ltd.)

(Antigen Peptide)
    OVAp (OVA peptide, 8-amino acid peptide having the sequence Ser Ile Ile Asn Phe Glu Lys Leu (SEQ ID No: 16))
    Survivin-2B (survivin 2B peptide, cancer antigen peptide)
    GPC3 (GPC3 peptide, cancer antigen peptide)
    HER2/neu_A24 (HER2/neu_A24 peptide, cancer antigen peptide)
    MAGE-A3_A24 (MAGE3_A24 peptide, cancer antigen peptide)
    IPEP87 (IPEP87 peptide, infectious pathogen antigen)
    PR1 (PR1 peptide, cancer antigen peptide)
    HER2_A02 (HER2/neu_A02 peptide, cancer antigen peptide)
    MAGE-A3_A02 (MAGE3_A02 peptide, cancer antigen peptide)
    HBVenv (HBVenv peptide, infectious pathogen antigen)
    HER2/neu_E75 (HER2/neu_E75 peptide, cancer antigen peptide)
    MUC1 (MUC1 peptide, cancer antigen peptide)

(Helper Peptide)
    Peptide-25 (Pep25)
    Peptide-25B (Pep25B)
    PADRE

<Evaluation 1>

The creams for transdermal administration obtained in the examples and comparative examples were evaluated as follows.

(Evaluation of Cellular Immunity Inducing Effect)

According to the procedure described below, the cream for transdermal administration was used to carry out a mouse immunity test using an animal model for immunological evaluation. Subsequently, the level of induction of antigen-specific cellular immunity was evaluated by ELISPOT assay.

(1) Animal Model for Immunological Evaluation

The "animal model for immunological evaluation" herein refers to an animal model for evaluating the immunity inducing properties of a vaccine pharmaceutical composition (in the present case, a cream for transdermal administration), and specifically refers to an animal model for evaluating the level of the cellular immunity induced by the cream for transdermal administration.

In consideration of the compatibility between the antigen in the cream for transdermal administration and MHC class I molecules of the animal, the animal model used for immunological evaluation was an animal with which induction of the cellular immunity by the antigen in the cream for transdermal administration can be evaluated.

Specifically, in a case where the antigen was a HLA-A*24-type MHC class 1 restriction peptide, the animal used for the evaluation was a BALB/c mouse. In a case where the antigen was a HLA-A*02-type MHC restriction peptide, the animal used was a genetically altered mouse with which induction of the cellular immunity by the HLA-A*02-type MHC restriction peptide can be evaluated. In a case where the antigen was another HLA-type MHC restriction peptide, the animal used was an animal with which induction of the cellular immunity by that HLA-type MHC restriction peptide can be evaluated. In the case of a protein antigen, the animal used was an animal having a MHC compatible with a class 1 epitope corresponding to the cellular immunity intended to be induced among class 1 epitopes contained in the amino acid sequence of the protein antigen.

(2) Mouse Immunity Test of Creams for Transdermal Administration

Examples 1 to 64, Comparative Examples 1 to 51

According to Tables 1 to 4 and 6, a mouse was prepared and its back was shaved. After a certain rearing period for recovery from skin damage caused by the shaving, 4 mg of the cream for transdermal administration was administered to the skin of the back for 24 hours and then removed the cream therefrom. The mouse was reared for six days. Six days after the administration, the spleen was extracted, and a spleen cell suspension was prepared. Spleen cells ($5\times10^5$ cells/well) and an antigen peptide (100 μM) together with a culture fluid were poured into wells of an ELISPOT plate on which an anti-mouse IFN-γ antibody was immobilized, and co-cultured under the culture conditions of 37° C. and 5% $CO_2$ for 20 hours. The number of IFN-γ-producing cell spots was evaluated by the ELISPOT assay. Tables 1 to 4 and 6 show the number of IFN-γ-producing cell spots as the "immunity result". FIG. 1 shows the immunity results of Comparative Example 2 (w/o Adjuvant) and Examples 1 to 10.

TABLE 1

| | Dosage form | Antigen Name | Antigen Amount [wt %] | Bisphosphonate Name | Bisphosphonate Amount [wt %] | Helper peptide Name | Helper peptide Amount [wt %] | Immunological evaluation mouse | Immunity result |
|---|---|---|---|---|---|---|---|---|---|
| Comparative Example 1 | Cream | OVAp | 2.5 | — | — | Pep25 | — | C57BL/6 | 2.5 |
| Comparative Example 2 | Cream | OVAp | 2.5 | — | — | Pep25 | 1 | C57BL/6 | 7.0 |
| Example 1 | Cream | OVAp | 2.5 | Etidronate | 2 | Pep25 | 1 | C57BL/6 | 33.0 |
| Example 2 | Cream | OVAp | 2.5 | Clodronate | 2 | Pep25 | 1 | C57BL/6 | 30.8 |
| Example 3 | Cream | OVAp | 2.5 | Tiludronate | 2 | Pep25 | 1 | C57BL/6 | 37.5 |
| Example 4 | Cream | OVAp | 2.5 | Pamidronate | 1 | Pep25 | 1 | C57BL/6 | 78.8 |
| Example 5 | Cream | OVAp | 2.5 | Alendronate | 1 | Pep25 | 1 | C57BL/6 | 135.5 |
| Example 6 | Cream | OVAp | 2.5 | Ibandronate | 1 | Pep25 | 1 | C57BL/6 | 124.3 |
| Example 7 | Cream | OVAp | 2.5 | Neridronate | 1 | Pep25 | 1 | C57BL/6 | 171.3 |
| Example 8 | Cream | OVAp | 2.5 | Zoledronate | 0.5 | Pep25 | 1 | C57BL/6 | 130.5 |
| Example 9 | Cream | OVAp | 2.5 | Risedronate | 0.5 | Pep25 | 1 | C57BL/6 | 158.0 |
| Example 10 | Cream | OVAp | 2.5 | Minodronate | 0.5 | Pep25 | 1 | C57BL/6 | 198.8 |
| Example 11 | Cream | OVAp | 2.5 | Alendronate | 1 | — | — | C57BL/6 | 64.2 |
| Example 12 | Cream | OVAp | 2.5 | Neridronate | 1 | — | — | C57BL/6 | 82.4 |
| Example 13 | Cream | OVAp | 2.5 | Zoledronate | 0.5 | — | — | C57BL/6 | 75.6 |
| Example 14 | Cream | OVAp | 2.5 | Risedronate | 0.5 | — | — | C57BL/6 | 90.6 |
| Example 15 | Cream | OVAp | 2.5 | Minodronate | 0.5 | — | — | C57BL/6 | 97.8 |

TABLE 2

| | Dosage form | Antigen Name | Antigen Amount [wt %] | Bisphosphonate Name | Bisphosphonate Amount [wt %] | Antioxidant Name | Antioxidant Amount [wt %] | Helper peptide Name | Helper peptide Amount [wt %] | Immunological evaluation mouse | Immunity result |
|---|---|---|---|---|---|---|---|---|---|---|---|
| Comparative Example 3 | Cream | OVAp | 2.5 | — | — | Sodium nitrite | 1 | Pep25 | 1 | C57BL/6 | 6.5 |
| Comparative Example 4 | Cream | OVAp | 2.5 | — | — | Ascorbic acid | 1 | Pep25 | 1 | C57BL/6 | 6.5 |
| Comparative Example 5 | Cream | OVAp | 2.5 | — | — | Sodium hydrogen sulfite | 1 | Pep25 | 1 | C57BL/6 | 7.0 |
| Comparative Example 6 | Cream | OVAp | 2.5 | — | — | Cysteine hydrochloride | 1 | Pep25 | 1 | C57BL/6 | 5.8 |
| Comparative Example 7 | Cream | OVAp | 2.5 | — | — | Citric acid hydrate | 1 | Pep25 | 1 | C57BL/6 | 7.3 |

TABLE 2-continued

| | Dosage form | Antigen Name | Antigen Amount [wt %] | Bisphosphonate Name | Bisphosphonate Amount [wt %] | Antioxidant Name | Antioxidant Amount [wt %] | Helper peptide Name | Helper peptide Amount [wt %] | Immunological evaluation mouse | Immunity result |
|---|---|---|---|---|---|---|---|---|---|---|---|
| Comparative Example 8 | Cream | OVAp | 2.5 | — | — | BHT | 1 | Pep25 | 1 | C57BL/6 | 6.0 |
| Comparative Example 9 | Cream | OVAp | 2.5 | — | — | Soybean lecithin | 1 | Pep25 | 1 | C57BL/6 | 7.8 |
| Comparative Example 10 | Cream | OVAp | 2.5 | — | — | Tocopherol | 1 | Pep25 | 1 | C57BL/6 | 6.3 |
| Comparative Example 11 | Cream | OVAp | 2.5 | — | — | Sodium pyrosulfite | 1 | Pep25 | 1 | C57BL/6 | 5.3 |
| Comparative Example 12 | Cream | OVAp | 2.5 | — | — | BHA | 1 | Pep25 | 1 | C57BL/6 | 6.3 |
| Comparative Example 13 | Cream | OVAp | 2.5 | — | — | 1,3-butylene glycol | 1 | Pep25 | 1 | C57BL/6 | 6.0 |
| Comparative Example 14 | Cream | OVAp | 2.5 | — | — | Benzotriazole | 1 | Pep25 | 1 | C57BL/6 | 5.5 |
| Comparative Example 15 | Cream | OVAp | 2.5 | — | — | Propyl gallate | 1 | Pep25 | 1 | C57BL/6 | 7.0 |
| Comparative Example 16 | Cream | OVAp | 2.5 | — | — | 2-MBI | 1 | Pep25 | 1 | C57BL/6 | 15.0 |
| Example 16 | Cream | OVAp | 2.5 | Zoledronate | 0.5 | Sodium nitrite | 0.5 | Pep25 | 1 | C57BL/6 | 201.3 |
| Example 17 | Cream | OVAp | 2.5 | Zoledronate | 0.5 | Ascorbic acid | 0.5 | Pep25 | 1 | C57BL/6 | 175.0 |
| Example 18 | Cream | OVAp | 2.5 | Zoledronate | 0.5 | Sodium hydrogen sulfite | 0.5 | Pep25 | 1 | C57BL/6 | 189.8 |
| Example 19 | Cream | OVAp | 2.5 | Zoledronate | 0.5 | Cysteine hydrochloride | 0.5 | Pep25 | 1 | C57BL/6 | 166.3 |
| Example 20 | Cream | OVAp | 2.5 | Zoledronate | 0.5 | Citric acid hydrate | 0.5 | Pep25 | 1 | C57BL/6 | 163.3 |
| Example 21 | Cream | OVAp | 2.5 | Zoledronate | 0.5 | BHT | 0.5 | Pep25 | 1 | C57BL/6 | 201.3 |
| Example 22 | Cream | OVAp | 2.5 | Zoledronate | 0.5 | Soybean lecithin | 0.5 | Pep25 | 1 | C57BL/6 | 234.3 |
| Example 23 | Cream | OVAp | 2.5 | Zoledronate | 0.5 | Tocopherol | 0.5 | Pep25 | 1 | C57BL/6 | 160.5 |
| Example 24 | Cream | OVAp | 2.5 | Zoledronate | 0.5 | Sodium pyrosulfite | 0.5 | Pep25 | 1 | C57BL/6 | 208.3 |
| Example 25 | Cream | OVAp | 2.5 | Zoledronate | 0.5 | BHA | 0.5 | Pep25 | 1 | C57BL/6 | 285.3 |
| Example 26 | Cream | OVAp | 2.5 | Zoledronate | 0.5 | 1,3-butylene glycol | 0.5 | Pep25 | 1 | C57BL/6 | 168.0 |
| Example 27 | Cream | OVAp | 2.5 | Zoledronate | 0.5 | Benzatriazole | 0.5 | Pep25 | 1 | C57BL/6 | 161.0 |
| Example 28 | Cream | OVAp | 2.5 | Zoledronate | 0.5 | Propyl gallate | 0.5 | Pep25 | 1 | C57BL/6 | 176.3 |
| Example 29 | Cream | OVAp | 2.5 | Zoledronate | 0.5 | 2-MBI | 0.5 | Pep25 | 1 | C57BL/6 | 229.3 |

TABLE 3

| | Dosage form | Antigen Name | Antigen Amount [wt %] | Bisphosphonate Name | Bisphosphonate Amount [wt %] | Anti-inflammatory drug Name | Anti-inflammatory drug Amount [wt %] | Helper peptide Name | Helper peptide Amount [wt %] | Immunological evaluation mouse | Immunity result |
|---|---|---|---|---|---|---|---|---|---|---|---|
| Comparative Example 17 | Cream | OVAp | 2.5 | — | — | Naringenin | 5 | Pep25 | 1 | C57BL/6 | 8.5 |
| Comparative Example 18 | Cream | OVAp | 2.5 | — | — | Epicatechin | 5 | Pep25 | I | C57BL/6 | 5.0 |
| Comparative Example 19 | Cream | OVAp | 2.5 | — | — | Apigenin | 5 | Pep25 | | C57BL/6 | 7.8 |
| Comparative Example 20 | Cream | OVAp | 2.5 | — | — | Chrysin | 5 | Pep25 | I | C57BL/6 | 7.0 |
| Comparative Example 21 | Cream | OVAp | 2.5 | — | — | Myricetin | 5 | Pep25 | 1 | C57BL/6 | 7.8 |
| Comparative Example 22 | Cream | OVAp | 2.5 | — | — | Rutin | 5 | Pep25 | I | C57BL/6 | 5.8 |
| Comparative Example 23 | Cream | OVAp | 2.5 | — | — | Genistein | 5 | Pep25 | 1 | C57BL/6 | 4.5 |
| Comparative Example 24 | Cream | OVAp | 2.5 | — | — | Nobiletin | 5 | Pep25 | 1 | C57BL/6 | 4.8 |
| Comparative Example 25 | Cream | OVAp | 2.5 | — | — | Curcumin | 5 | Pep25 | I | C57BL/6 | 10.0 |
| Comparative Example 26 | Cream | OVAp | 2.5 | — | — | Resveratrol | 5 | Pep25 | 1 | C57BL/6 | 8.0 |
| Comparative Example 27 | Cream | OVAp | 2.5 | — | — | Coumarin | 5 | Pep25 | 1 | C57BL/6 | 8.0 |
| Comparative Example 28 | Cream | OVAp | 2.5 | — | — | Berberine | 5 | Pep25 | 1 | C57BL/6 | 11.3 |
| Comaprative Example 29 | Cream | OVAp | 2.5 | — | — | Glycyrrhetinic acid | 5 | Pep25 | 1 | C57BL/6 | 11.3 |
| Example 30 | Cream | OVAp | 2.5 | Zoledronate | 0.5 | Naringenin | 4.5 | Pep25 | 1 | C57BL/6 | 195.5 |
| Example 31 | Cream | OVAp | 2.5 | Zoledronate | 0.5 | Epicatechin | 4.5 | Pep25 | 1 | C57BL/6 | 220.8 |
| Example 32 | Cream | OVAp | 2.5 | Zoledronate | 0.5 | Apigenin | 4.5 | Pep25 | 1 | C57BL/6 | 160.5 |

TABLE 3-continued

|  | Dosage form | Antigen Name | Antigen Amount [wt %] | Bisphosphonate Name | Bisphosphonate Amount [wt %] | Anti-inflammatory drug Name | Anti-inflammatory drug Amount [wt %] | Helper peptide Name | Helper peptide Amount [wt %] | Immunological evaluation mouse | Immunity result |
|---|---|---|---|---|---|---|---|---|---|---|---|
| Example 33 | Cream | OVAp | 2.5 | Zoledronate | 0.5 | Chrysin | 4.5 | Pep25 | 1 | C57BL/6 | 238.8 |
| Example 34 | Cream | OVAp | 2.5 | Zoledronate | 0.5 | Myricetin | 4.5 | Pep25 | 1 | C57BL/6 | 243.0 |
| Example 35 | Cream | OVAp | 2,5 | Zoledronate | 0.5 | Rutin | 4.5 | Pep25 | 1 | C57BL/6 | 198.5 |
| Example 36 | Cream | OVAp | 2:5 | Zoledronate | 0.5 | Genistein | 4.5 | Pep25 | 1 | C57BL/6 | 162.8 |
| Example 37 | Cream | OVAp | 2,5 | Zoledronate | 0.5 | Nobiletin | 4.5 | Pep25 | 1 | C57BL/6 | 185.8 |
| Example 38 | Cream | OVAp | 2.5 | Zoledronate | 0.5 | Curcumin | 4.5 | Pep25 | 1 | C57BL/6 | 163.0 |
| Example 39 | Cream | OVAp | 2.5 | Zoledronate | 0.5 | Resveratrol | 4.5 | Pep25 | 1 | C57BL/6 | 256.3 |
| Example 40 | Cream | OVAp | 2.5 | Zoledronate | 0.5 | Coumarin | 4.5 | Pep25 | 1 | C57BL/6 | 270.3 |
| Example 41 | Cream | OVAp | 2.5 | Zoledronate | 0.5 | Berberine | 4.5 | Pep25 | 1 | C57BL/6 | 191.5 |
| Example 42 | Cream | OVAp | 2.5 | Zoledronate | 0.5 | Glycyrrhetinic acid | 4.5 | Pep25 | 1 | C57BL/6 | 279.5 |

TABLE 4

|  | Dosage Form | Antigen Name | Antigen Amount [wt %] | Bisphosphonate Name | Bisphosphonate Amount [wt %] | COX inhibitor (anti-inflammatory drug) Name | COX inhibitor Amount [wt %] | Helper peptide Name | Helper peptide Amount [wt %] | Immunological evaluation mouse | Immunity result |
|---|---|---|---|---|---|---|---|---|---|---|---|
| Comparative Example 30 | Cream | OVAp | 2.5 | — | — | Etodolac | 5 | Pep25 | 1 | C57BL/6 | 26.8 |
| Comparative Example 31 | Cream | OVAp | 2.5 | — | — | Loxoprofen | 5 | Pep25 | 1 | C57BL/6 | 26.3 |
| Comparative Example 32 | Cream | OVAp | 2.5 | — | — | Diclofenac | 5 | Pep25 | 1 | C57BL/6 | 24.8 |
| Comparative Example 33 | Cream | OVAp | 2.5 | — | — | Celecoxib | 5 | Pep25 | 1 | C57BL/6 | 28.5 |
| Comparative Example 34 | Cream | OVAp | 2.5 | — | — | Valdepoxib | 5 | Pep25 | 1 | C57BL/6 | 30.5 |
| Comparative Example 35 | Cream | OVAp | 2.5 | — | — | Piroxicam | 5 | Pep25 | 1 | C57BL/6 | 14.3 |
| Comparative Example 36 | Cream | OVAp | 2.5 | — | — | Aspirin | 5 | Pep25 | 1 | C57BL/6 | 6.5 |
| Comparative Example 37 | Cream | OVAp | 2.5 | — | — | Indomethacin | 5 | Pep25 | 1 | C57BL/6 | 15.5 |
| Comparative Example 38 | Cream | OVAp | 2.5 | — | — | Ketoprofen | 5 | Pep25 | 1 | C57BL/6 | 18.0 |
| Comparative Example 39 | Cream | OVAp | 2.5 | — | — | Ibuprofen |  | Pep25 | 1 | C57BL/6 | 11.8 |
| Comaprative Example 40 | Cream | OVAp | 2.5 | — | — | Naproxen | 5 | Pep25 | 1 | C57BL/6 | 16.5 |
| Example 43 | Cream | OVAp | 2.5 | Zoledronate | 0.5 | Etodolac | 4.5 | Pep25 | 1 | C57BL/6 | 195.3 |
| Example 44 | Cream | OVAp | 2.5 | Zoledronate | 0.5 | Loxoprofen | 4.5 | Pep25 | 1 | C57BL/6 | 243.3 |
| Example 45 | Cream | OVAp | 2.5 | Zoledronate | 0.5 | Diclofenac | 4.5 | Pep25 | 1 | C57BL/6 | 227.3 |
| Example 46 | Cream | OVAp | 2.5 | Zoledronate | 0.5 | Celecoxib | 4.5 | Pep25 | 1 | C57BL/6 | 231.0 |
| Example 47 | Cream | OVAp | 2.5 | Zoledronate | 0.5 | Valdecoxib | 4.5 | Pep25 | 1 | C57BL/6 | 242.8 |
| Example 48 | Cream | OVAp | 2.5 | Zoledronate | 0.5 | Piroxicam | 4.5 | Pep25 | 1 | C57BL/6 | 322.3 |
| Example 49 | Cream | OVAp | 2.5 | Zoledronate | 0.5 | Aspirin | 4.5 | Pep25 | 1 | C57BL/6 | 428.3 |
| Example 50 | Cream | OVAp | 2.5 | Zoledronate | 0.5 | Indomethacin | 4.5 | Pep25 | 1 | C57BL/6 | 325.0 |
| Example 51 | Cream | OVAp | 2.5 | Zoledronate | 0.5 | Ketoprofen | 4.5 | Pep25 | 1 | C57BL/6 | 204.5 |
| Example 52 | Cream | OVAp | 2.5 | Zoledronate | 0.5 | Ibuprofen | 4.5 | Pep25 | 1 | C57BL/6 | 222.3 |
| Example 53 | Cream | OVAp | 2.5 | Zoledronate | 0.5 | Naproxen | 4.5 | Pep25 | 1 | C57BL/6 | 294.8 |

TABLE 5

|  | Additive | Amount [parts by weight] |
|---|---|---|
| Base cream | White Vaseline | 60.7 |
|  | Sorbitan monostearate | 0.7 |
|  | Isostearic acid | 12 |
|  | Benzyl alcohol | 2.4 |
|  | Cetanol | 2.4 |
|  | Stearyl alcohol | 3.5 |
|  | Polysorbate 60 | 3.5 |
|  | Concentrated glycerin | 2.4 |
|  | Purified water | 12.4 |
|  | Total | 100 |

TABLE 6

| | Dosage form | Antigen Name | Antigen Amount [wt %] | Bisphosphonate Name | Bisphosphonate Amount [wt %] | Helper peptide Name | Helper peptide Amount [wt %] | Immunological evaluation mouse | Immunity result Average value | Immunity result [cells/well] |
|---|---|---|---|---|---|---|---|---|---|---|
| Comparative Example 41 | Cream | Survivin-2B | 10 | — | — | Pep25B | 1 | BALB/c | 19.3 | $1 \times 10^6$ |
| Example 54 | Cream | Survivin-2B | 10 | Zoledronate | 0.5 | Pep25B | 1 | BALB/c | 188.8 | |
| Comparative Example 42 | Cream | GPC3 | 20 | — | — | Pep25B | 1 | BALB/c | 1.5 | $3 \times 10^6$ |
| Example 55 | Cream | GPC3 | 20 | Zoledronate | 0.5 | Pep25B | 1 | BALB/c | 19.0 | |
| Comparative Example 43 | Cream | HER2/neu_A24 | 5 | — | — | Pep25B | 1 | BALB/c | 31.0 | $1 \times 10^6$ |
| Example 56 | Cream | HER2/neu_A24 | 5 | Zoledronate | 0.5 | Pep25B | 1 | BALB/c | 236.8 | |
| Comparative Example 44 | Cream | MAGE-A3_A24 | 10 | — | — | Pep25B | 1 | BALB/c | 19.0 | $1 \times 10^6$ |
| Example 57 | Cream | MAGE-A3_A24 | 10 | Zoledronate | 0.5 | Pep25B | 1 | BALB/c | 215.3 | |
| Comparative Example 45 | Cream | IPEP87 | 10 | — | — | PADRE | 1 | Gene-altered | 25.8 | $1 \times 10^6$ |
| Example 58 | Cream | IPEP87 | 10 | Zoledronate | 0.5 | PADRE | 1 | Gene-altered | 291.5 | |
| Comparative Example 46 | Cream | PR1 | 10 | — | — | PADRE | 1 | Gene-altered | 15.3 | $1 \times 10^6$ |
| Example 59 | Cream | PR1 | 10 | Zoledronate | 0.5 | PADRE | 1 | Gene-altered | 186.3 | |
| Comparative Example 47 | Cream | HER2_A02 | 10 | — | — | PADRE | 1 | Gene-altered | 13.8 | $2 \times 10^6$ |
| Example 60 | Cream | HER2_A02 | 10 | Zoledronate | 0.5 | PADRE | 1 | Gene-altered | 186.0 | |
| Comparative Example 48 | Cream | MAGE-A3_A02 | 10 | — | — | PADRE | 1 | Gene-altered | 18.0 | $1 \times 10^6$ |
| Example 61 | Cream | MAGE-A3_A02 | 10 | Zoledronate | 0.5 | PADRE | 1 | Gene-altered | 214.5 | |
| Comparative Example 49 | Cream | HBVenv | 20 | — | — | PADRE | 1 | Gene-altered | 9.5 | $2 \times 10^6$ |
| Example 62 | Cream | HBVenv | 20 | Zoledronate | 0.5 | PADRE | 1 | Gene-altered | 120.8 | |
| Comparative Example 50 | Cream | HER2/neu_E75 | 10 | — | — | PADRE | 1 | Gene-altered | 14.5 | $2 \times 10^6$ |
| Example 63 | Cream | HER2/neu_E75 | 10 | Zoledronate | 0.5 | PADRE | 1 | Gene-altered | 188.3 | |
| Comparative Example 51 | Cream | MUC1 | 20 | — | — | PADRE | 1 | Gene-altered | 0.8 | $3 \times 10^6$ |
| Example 64 | Cream | MUC1 | 20 | Zoledronate | 0.5 | PADRE | 1 | Gene-altered | 18.3 | |

(3) Mouse Immunity Test of Tapes for Transdermal Administration

Examples 65 to 76, Comparative Examples 52 to 57

(Preparation of Tapes for Transdermal Administration)

A tape for transdermal administration having a composition shown in Table 7 was prepared. Specifically, an antigen peptide, a first cellular immunity induction promoter that is a bisphosphonate, and if necessary, a second cellular immunity induction promoter that is a helper peptide mentioned above were blended. To the mixture, an adhesive and an organic solvent (ethyl acetate when the adhesive is an acrylic, toluene when the adhesive is PIB) shown in Table 7 were added to obtain the total amount of the components and the adhesive after drying of the organic solvent of 100% by weight, and mixed to prepare an adhesive solution. The obtained adhesive solution was casted on a release liner to the thickness after drying of about 80 μm. The organic solvent was removed by drying, thereby forming an adhesive layer. The release liner used was a polyethylene terephthalate (PET) liner (thickness: 75 μm) subjected to silicon release treatment. The resulting adhesive layer was attached to a support, thereby preparing a tape for transdermal administration. The support used was a polyethylene terephthalate (PET) film (thickness: 25 μm).

The tape for transdermal administration was cut to give a piece with an area of 0.7 cm², and the piece was used as an administration sample in the immunity test. Upon administration, the release liner was removed.

(Adhesive)

Acrylic adhesive (an acrylic adhesive solution prepared by solution-polymerizing 75 parts of 2-ethylhexyl acrylate, 22 parts of N-vinyl-2-pyrrolidone, 3 parts of acrylic acid, and 0.2 parts of azobisisobutyronitrile in ethyl acetate at 60° C. in an inert gas atmosphere)

PIB adhesive (PIB adhesive solution prepared by dissolving 24 parts of polyisobutylene (Oppanol B200, Basf SE), 36 parts of polyisobutylene (Oppanol B12, Basf SE), and 40 parts of an alicyclic petroleum resin (ARKON P-100, Arakawa Chemical Industries, LTD.) in toluene)

<Evaluation 2>

The tapes for transdermal administration obtained in the examples and comparative examples were evaluated as follows.

(Evaluation on Cellular Immunity Inducing Effect)

The level of inducing the antigen-specific cellular immunity was evaluated in the same manner as in the evaluation of the creams for transdermal administration. Table 7 shows the results as the "Immunity result".

TABLE 7

| | Dosage form | Adhesive | Antigen Name | Antigen Amount [wt %] | Bisphosphonate Name | Bisphosphonate Amount [wt %] | Helper peptide Name | Helper peptide Amount [wt %] | Immunological evaluation mouse | Immunity result Average value | Immunity result [cells/well] |
|---|---|---|---|---|---|---|---|---|---|---|---|
| Comparative Example 52 | Tape | Acrylic | HER2/neu_E75 | 10 | — | — | PADRE | 1 | Gene-altered | 4.3 | $2 \times 10^6$ |
| Example 65 | Tape | Acrylic | HER2/neu_E75 | 10 | Zoledronate | 1 | — | — | Gene-altered | 23.5 | |
| Example 66 | Tape | Acrylic | HER2/nerr_E75 | 10 | Zoledronate | 1 | PADRE | 1 | Gene-altered | 49.8 | |
| Comparative Example 53 | Tape | PIB | HER2/neu_E75 | 10 | — | — | PADRE | 1 | Gene-altered | 5.3 | $2 \times 10^6$ |
| Example 67 | Tape | PIB | HER2/neu_E75 | 10 | Zoledronate | 1 | — | — | Gene-altered | 22.8 | |
| Example 68 | Tape | PIB | HER2/neu_E75 | 10 | Zoledronate | 1 | PADRE | 1 | Gene-altered | 52.0 | |
| Comparative Example 54 | Tape | Acrylic | IPEP87 | 10 | — | — | PADRE | 1 | Gene-altered | 5.8 | $2 \times 10^6$ |
| Example 69 | Tape | Acrylic | IPEP87 | 10 | Zoledronate | 1 | — | — | Gene-altered | 23.5 | |
| Example 70 | Tape | Acrylic | IPEP87 | 10 | Zoledronate | 1 | PADRE | 1 | Gene-altered | 53.5 | |
| Comparative Example 55 | Tape | PIB | IPEP87 | 10 | — | — | PADRE | 1 | Gene-altered | 8.5 | $2 \times 10^6$ |
| Example 71 | Tape | PIB | IPEP87 | 10 | Zoledronate | 1 | — | — | Gene-altered | 33.3 | |
| Example 72 | Tape | PIB | IPEP87 | 10 | Zoledronate | 1 | PADRE | 1 | Gene-altered | 69.8 | |
| Comparative Example 56 | Tape | Acrylic | MAGE-A3_A02 | 10 | — | — | PADRE | 1 | Gene-altered | 10.5 | $2 \times 10^6$ |
| Example 73 | Tape | Acrylic | MAGE-A3_A02 | 10 | Zoledronate | 1 | — | — | Gene--altered | 32.8 | |
| Example 74 | Tape | Acrylic | MAGE-A3_A02 | 10 | Zoledronate | 1 | PADRE | 1 | Gene-altered | 68.0 | |
| Comparative Example 57 | Tape | PIB | MAGE-A3_A02 | 10 | — | — | PADRE | 1 | Gene-altered | 9.5 | $2 \times 10^6$ |
| Example 75 | Tape | PIB | MAGE-A3_A02 | 10 | Zoledronate | 1 | — | — | Gene-altered | 36.3 | |
| Example 76 | Tape | PIB | MAGE-A3_A02 | 10 | Zoledronate | 1 | PADRE | 1 | Gene-altered | 73.5 | |

(4) Mouse Immunity Test of Creams for Transdermal Administration (Minimally Invasive Administration)

Examples 77 to 91, Comparative Examples 58 to 59

Creams for transdermal administration having a composition shown in Table 8 were prepared in the same manner as in the case of the creams for transdermal administration shown in Table 1. A mouse was prepared and its right back was shaved. Corneum exfoliation treatment was performed thereon five times using an OPP tape (EZDunplon No. 3301EZ) produced by Nitto Denko Corporation. The cream was administered to the treated skin (minimally invasive administration). Twenty-four hours later, the cream for transdermal administration was removed, and the mouse was reared for six days. Six days after the administration, the spleen was extracted, and antigen-specific IFN-γ-producing cells were analyzed by the ELISPOT assay.

Also by an immunization method utilizing minimally invasive administration as shown in Table 8, cellular immunity specific to the administered antigen can be induced.

TABLE 8

| | Dosage form | Antigen Name | Antigen Amount [wt %] | Bisphosphonate Name | Bisphosphonate Amount [wt %] | Helper peptide Name | Helper peptide Amount [wt %] | Immunological evaluation mouse |
|---|---|---|---|---|---|---|---|---|
| Comparative Example 58 | Cream | OVAp | 2.5 | — | — | Pep25 | — | C57BL/6 |
| Comparative Example 59 | Cream | OVAp | 2.5 | — | — | Pep25 | 1 | C57BL/6 |
| Example 77 | Cream | OVAp | 2.5 | Etidronate | 2 | Pep25 | 1 | C57BL/6 |
| Example 78 | Cream | OVAp | 2.5 | Clodronate | 2 | Pep25 | 1 | C57BL/6 |
| Example 79 | Cream | OVAp | 2.5 | Tiludronate | 2 | Pep25 | 1 | C57BL/6 |
| Example 80 | Cream | OVAp | 2.5 | Pamidronate | 1 | Pep25 | 1 | C57BL/6 |
| Example 81 | Cream | OVAp | 2.5 | Alendronate | 1 | Pep25 | 1 | C57BL/6 |
| Example 82 | Cream | OVAp | 2.5 | Ibandronate | 1 | Pep25 | 1 | C57BL/6 |
| Example 83 | Cream | OVAp | 2.5 | Neridronate | 1 | Pep25 | 1 | C57BL/6 |
| Example 84 | Cream | OVAp | 2.5 | Zoledronate | 0.5 | Pep25 | 1 | C57BL/6 |
| Example 85 | Cream | OVAp | 2.5 | Risedronate | 0.5 | Pep25 | 1 | C57BL/6 |
| Example 86 | Cream | OVAp | 2.5 | Minodronate | 0.5 | Pep25 | 1 | C57BL/6 |
| Example 87 | Cream | OVAp | 2.5 | Alendronate | 1 | — | — | C57BL/6 |
| Example 88 | Cream | OVAp | 2.5 | Neridronate | 1 | — | — | C57BL/6 |
| Example 89 | Cream | OVAp | 2.5 | Zoledronate | 0.5 | — | — | C57BL/6 |
| Example 90 | Cream | OVAp | 2.5 | Risedronate | 0.5 | — | — | C57BL/6 |
| Example 91 | Cream | OVAp | 2.5 | Minodronate | 0.5 | — | — | C57BL/6 |

INDUSTRIAL APPLICABILITY

The vaccine pharmaceutical composition of the present invention is universally usable for induction of cellular immunity against various antigens, exerts a high cellular immunity inducing effect, and is suitably used for transdermal administration or transmucosal administration.

The invention claimed is:

1. A vaccine pharmaceutical composition for inducing cellular immunity, comprising:
   an antigen;
   a first cellular immunity induction promoter that is a bisphosphonate; and
   a second cellular immunity induction promoter that is a helper peptide selected from the group consisting of Peptide-25, Peptide-25B, and PADRE.

2. The vaccine pharmaceutical composition according to claim 1, wherein the first cellular immunity induction promoter that is a bisphosphonate is at least one selected from the group consisting of etidronate, clodronate, tiludronate, pamidronate, alendronate, ibandronate, neridronate, zoledronate, risedronate, and minodronate.

3. The vaccine pharmaceutical composition according to claim 2, further comprising at least one of an antioxidant and an anti-inflammatory drug.

4. The vaccine pharmaceutical composition according to claim 3, wherein the vaccine pharmaceutical composition comprises at least one antioxidant selected from the group consisting of sodium nitrite, ascorbic acid, sodium hydrogen sulfite, cysteine hydrochloride, citric acid hydrate, dibutylhydroxytoluene, soybean lecithin, tocopherol, sodium pyrosulfite, dibutylhydroxyanisole, 1,3-butylene glycol, benzotriazole, propyl gallate, and 2-mercaptobenzimidazole.

5. The vaccine pharmaceutical composition according to claim 3, wherein the vaccine pharmaceutical composition comprises at least one anti-inflammatory drug selected from the group consisting of polyphenols, alkaloids, and phospholipase A2 inhibitors.

6. The vaccine pharmaceutical composition according to claim 3, wherein the vaccine pharmaceutical composition comprises at least one anti-inflammatory drug that is a cyclooxygenase inhibitor.

7. The vaccine pharmaceutical composition according to claim 6, wherein the cyclooxygenase inhibitor is at least one selected from the group consisting of cyclooxygenase non-selective inhibitors, cyclooxygenase-1 selective inhibitors, and cyclooxygenase-2 selective inhibitors.

8. The vaccine pharmaceutical composition according to claim 1, wherein the helper peptide is PADRE.

9. The vaccine pharmaceutical composition according to claim 1, wherein the dosage form of the vaccine pharmaceutical composition is a tape or a cream.

10. The vaccine pharmaceutical composition according to claim 1, wherein:
    the vaccine pharmaceutical composition is structured and arranged to be administered to a body surface for transdermal administration; and
    a dosage form of the vaccine pharmaceutical composition is at least one selected from the group consisting of a liniment, a lotion, an aerosol, a gel, a tape, a poultice, an ointment, a plaster, and a cream.

11. A method for inducing cellular immunity in a subject comprising administering to the subject a vaccine pharmaceutical composition comprising:
    an antigen;
    a first cellular immunity induction promoter that is a bisphosphonate; and
    a second cellular immunity induction promoter that is a helper peptide selected from the group consisting of Peptide-25, Peptide-25B, and PADRE, wherein the administration induces a cellular immune response in the subject.

12. The method for inducing cellular immunity according to claim 11, wherein:
the vaccine pharmaceutical composition is structured and arranged to be administered to a body surface for transdermal administration; and
a dosage form of the vaccine pharmaceutical composition is at least one selected from the group consisting of a liniment, a lotion, an aerosol, a gel, a tape, a poultice, an ointment, a plaster, and a cream.

13. The method for inducing cellular immunity according to claim 11, wherein the first cellular immunity induction promoter that is a bisphosphonate is at least one selected from the group consisting of etidronate, clodronate, tiludronate, pamidronate, alendronate, ibandronate, neridronate, zoledronate, risedronate, and minodronate.

14. The method for inducing cellular immunity according to claim 11, wherein the vaccine pharmaceutical composition comprises at least one of an antioxidant and an anti-inflammatory drug.

15. The method for inducing cellular immunity according to claim 14, wherein the vaccine pharmaceutical composition comprises at least one antioxidant selected from the group consisting of sodium nitrite, ascorbic acid, sodium hydrogen sulfite, cysteine hydrochloride, citric acid hydrate, dibutylhydroxytoluene, soybean lecithin, tocopherol, sodium pyrosulfite, dibutylhydroxyanisole, 1,3-butylene glycol, benzotriazole, propyl gallate, and 2-mercaptobenzimidazole.

16. The method for inducing cellular immunity according to claim 14, wherein the vaccine pharmaceutical composition comprises at least one anti-inflammatory drug selected from the group consisting of polyphenols, alkaloids, and phospholipase A2 inhibitors.

17. The method for inducing cellular immunity according to claim 14, wherein the vaccine pharmaceutical composition comprises at least one anti-inflammatory drug that is a cyclooxygenase inhibitor.

18. The method for inducing cellular immunity according to claim 17, wherein the cyclooxygenase inhibitor is at least one selected from the group consisting of cyclooxygenase non-selective inhibitors, cyclooxygenase-1 selective inhibitors, and cyclooxygenase-2 selective inhibitors.

19. The method for inducing cellular immunity according to claim 11, comprising administering the vaccine pharmaceutical composition to a body surface of the subject.

20. The method for inducing cellular immunity according to claim 11, wherein the helper peptide is PADRE.

* * * * *